(12) United States Patent
Kitano

(10) Patent No.: US 11,690,588 B2
(45) Date of Patent: Jul. 4, 2023

(54) PROCESSING APPARATUS, METHOD OF OPERATING PROCESSING APPARATUS, AND OPERATION PROGRAM FOR PROCESSING APPARATUS

(71) Applicant: FUJIFILM CORPORATION, Tokyo (JP)

(72) Inventor: Koichi Kitano, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 41 days.

(21) Appl. No.: 17/335,079

(22) Filed: Jun. 1, 2021

(65) Prior Publication Data

US 2021/0378622 A1    Dec. 9, 2021

(30) Foreign Application Priority Data

Jun. 5, 2020    (JP) .................................. 2020-098879

(51) Int. Cl.
*A61B 6/00* (2006.01)
*G01S 17/08* (2006.01)
*A61B 6/02* (2006.01)

(52) U.S. Cl.
CPC .............. *A61B 6/544* (2013.01); *A61B 6/488* (2013.01); *A61B 6/5211* (2013.01); *A61B 6/585* (2013.01);
(Continued)

(58) Field of Classification Search
CPC ........... A61B 6/025; A61B 6/488; A61B 6/52; A61B 6/5211; A61B 6/5258; A61B 6/544; A61B 6/585

See application file for complete search history.

(56) References Cited

U.S. PATENT DOCUMENTS

2001/0012330 A1*  8/2001  Ogura .................... A61B 6/588
                                                            378/162
2008/0260232 A1* 10/2008  Ohara .................... G06T 5/002
                                                            348/E5.089
(Continued)

FOREIGN PATENT DOCUMENTS

JP      H04-241842 A    8/1992
JP      2010-057573 A   3/2010
(Continued)

OTHER PUBLICATIONS

English language translation of the following: Office action dated Mar. 22, 2023 from the JPO in a Japanese patent application No. 2020-098879 corresponding to the instant patent application. This office action translation is submitted now in order to supplement the understanding of the cited references which are being disclosed in the instant Information Disclosure Statement.

*Primary Examiner* — Dani Fox
*Assistant Examiner* — Soorena Kefayati
(74) *Attorney, Agent, or Firm* — Solaris Intellectual Property Group, PLLC

(57) ABSTRACT

A body thickness conversion unit converts a body thickness from a distance image imaged by a distance measurement camera to acquire the body thickness. A setting unit sets a gradation transformation function for use in gradation transformation processing to a radiographic image corresponding to the body thickness. A radiographic image acquisition unit acquires the radiographic image output from a radiation detector in radioscopy. A gradation transformation processing unit starts the gradation transformation processing with the gradation transformation function set by the setting unit.

10 Claims, 26 Drawing Sheets

(52) U.S. Cl.
CPC ............. *A61B 6/025* (2013.01); *A61B 6/5258* (2013.01); *G01S 17/08* (2013.01)

(56) References Cited

U.S. PATENT DOCUMENTS

| | | | |
|---|---|---|---|
| 2009/0003670 A1 | 1/2009 | Gu et al. | |
| 2009/0279764 A1* | 11/2009 | Kaji | A61B 6/463 382/132 |
| 2010/0098215 A1* | 4/2010 | Takahashi | A61B 6/06 378/98 |
| 2010/0329533 A1* | 12/2010 | Omi | H04N 5/32 382/132 |
| 2012/0257809 A1* | 10/2012 | Miyamoto | G06T 5/50 382/132 |
| 2014/0341350 A1* | 11/2014 | Muroi | A61B 6/504 378/62 |
| 2015/0093013 A1* | 4/2015 | Morita | G16H 50/20 382/132 |
| 2015/0313558 A1* | 11/2015 | Melman | A61B 6/5205 378/62 |
| 2016/0019701 A1 | 1/2016 | Visser et al. | |
| 2016/0089094 A1* | 3/2016 | Kawamura | A61B 6/44 378/62 |
| 2016/0140721 A1* | 5/2016 | Kawamura | A61B 6/544 382/132 |
| 2016/0148355 A1* | 5/2016 | Nakamura | A61B 6/4233 382/132 |
| 2016/0192892 A1* | 7/2016 | Guez | A61B 6/469 378/147 |
| 2016/0206264 A1* | 7/2016 | Fukuda | A61B 6/4452 |
| 2016/0220213 A1* | 8/2016 | Miyamoto | A61B 6/42 |
| 2016/0235384 A1* | 8/2016 | Enomoto | A61B 6/4291 |
| 2016/0253455 A1* | 9/2016 | Hasegawa | G16H 30/40 705/2 |
| 2016/0267630 A1* | 9/2016 | Naito | G06T 5/008 |
| 2016/0302752 A1* | 10/2016 | Ito | G06T 5/40 |
| 2016/0331334 A1* | 11/2016 | Imamura | A61B 6/06 |
| 2016/0349195 A1* | 12/2016 | Inoue | G01N 23/04 |
| 2016/0354052 A1* | 12/2016 | Kawanishi | A61B 6/5282 |
| 2017/0055933 A1* | 3/2017 | Kawamura | G16H 50/20 |
| 2017/0065244 A1* | 3/2017 | Taki | A61B 6/544 |
| 2017/0086770 A1* | 3/2017 | Morita | A61B 6/025 |
| 2017/0086777 A1* | 3/2017 | Kawamura | A61B 6/588 |
| 2017/0231593 A1* | 8/2017 | Fukuda | A61B 6/482 382/132 |
| 2017/0296133 A1* | 10/2017 | Katsumata | A61B 6/50 |
| 2018/0108118 A1* | 4/2018 | Takahashi | A61B 6/5235 |
| 2018/0116524 A1* | 5/2018 | Aoshima | A61B 6/4452 |
| 2018/0146937 A1* | 5/2018 | Nariyuki | A61B 6/4452 |
| 2019/0046128 A1* | 2/2019 | Yamazaki | A61B 5/0082 |
| 2020/0237332 A1* | 7/2020 | Wang | A61B 6/5241 |
| 2021/0161501 A1 | 6/2021 | Sendai | |

FOREIGN PATENT DOCUMENTS

| | | |
|---|---|---|
| JP | 2011-005050 A | 1/2011 |
| JP | 2015-167613 A | 9/2015 |
| JP | 2016-022095 A | 2/2016 |
| JP | 2016-067586 A | 5/2016 |
| JP | 2017-143943 A | 8/2017 |
| WO | 2010/097941 A1 | 9/2010 |
| WO | 2020/036225 A1 | 2/2020 |

* cited by examiner

FIG. 2
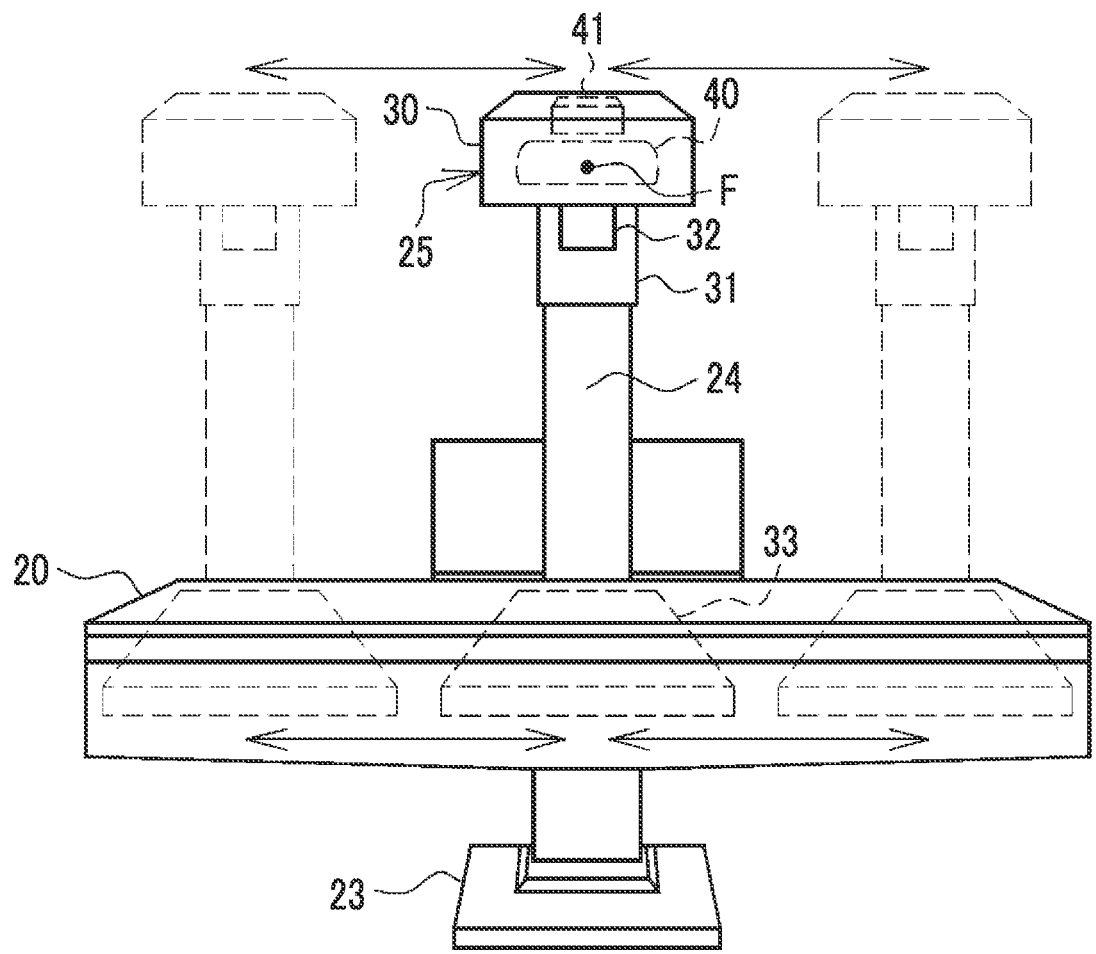
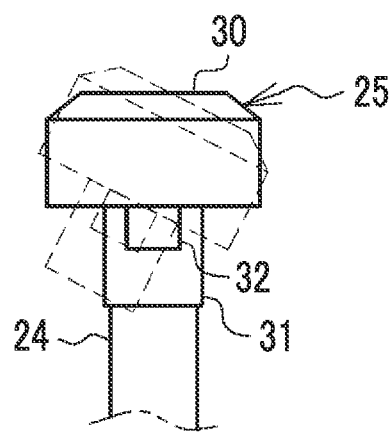
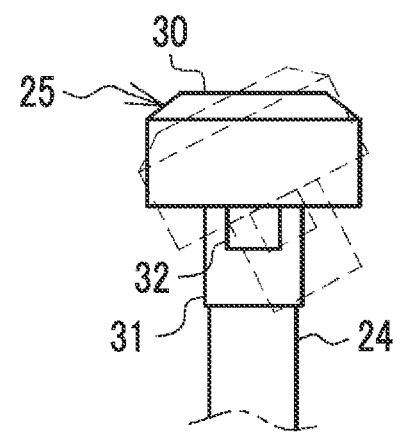
FIG. 3A          FIG. 3B

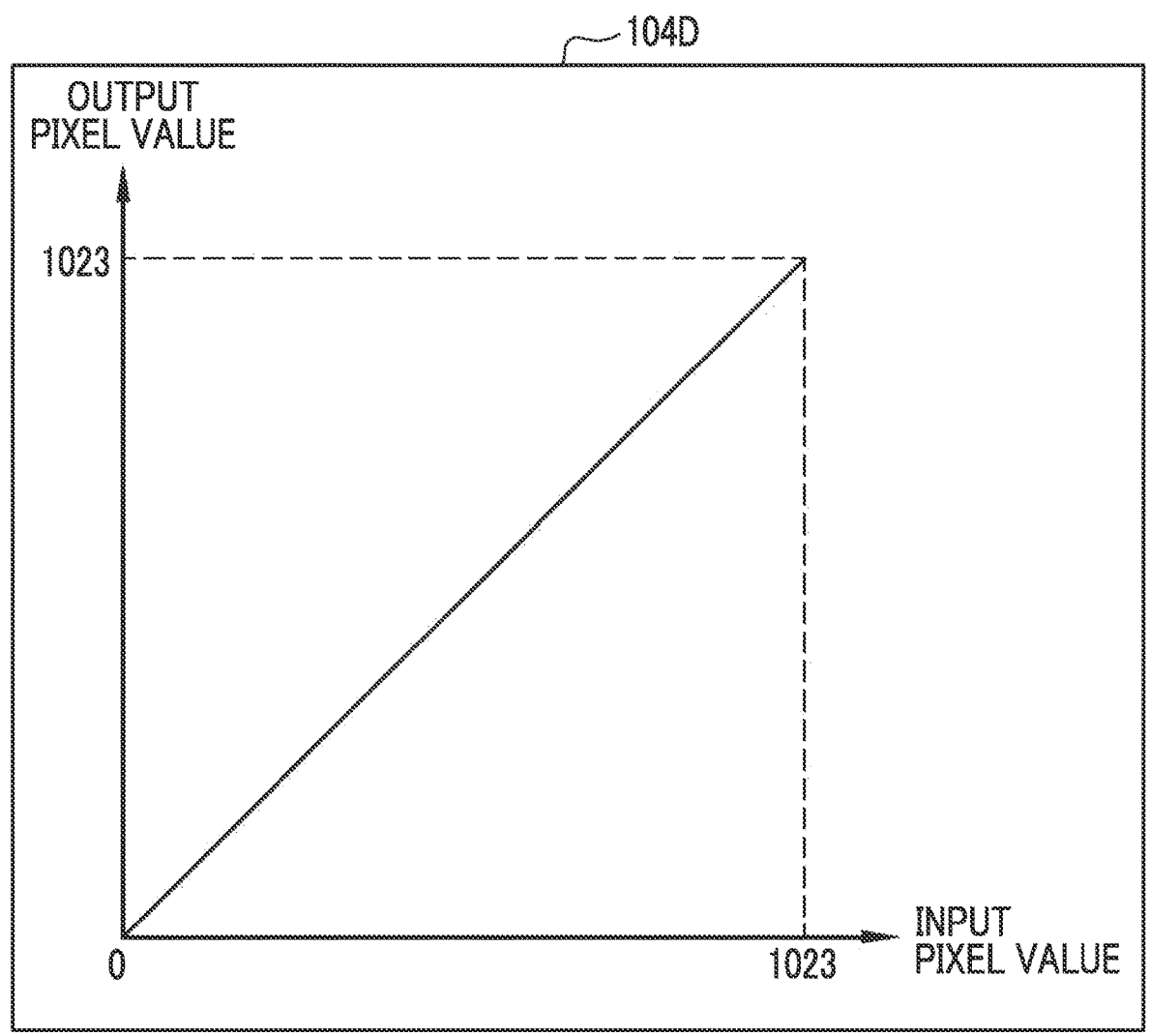

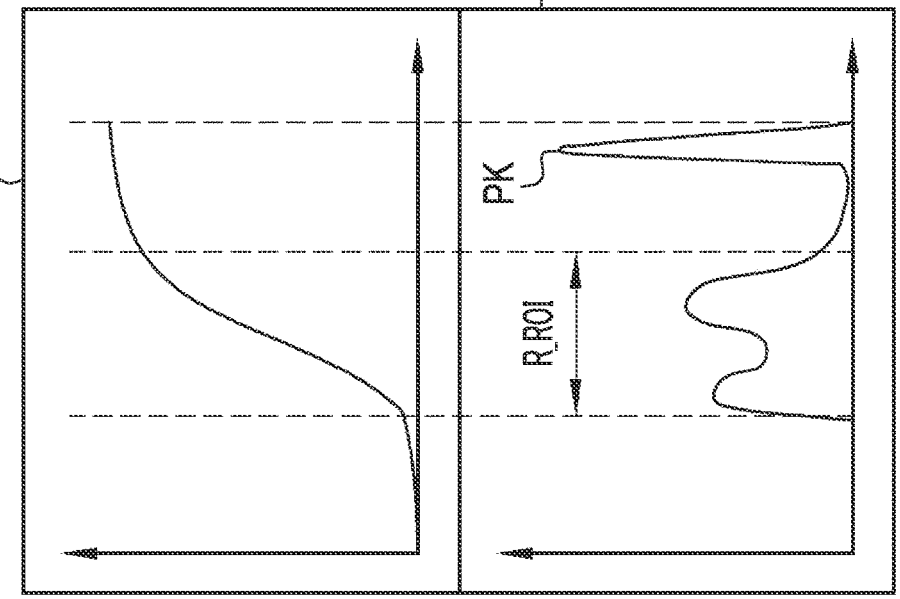
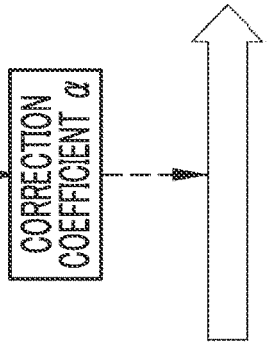
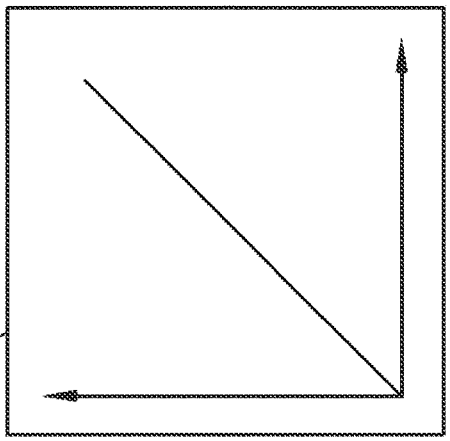
FIG. 16

FIG. 23
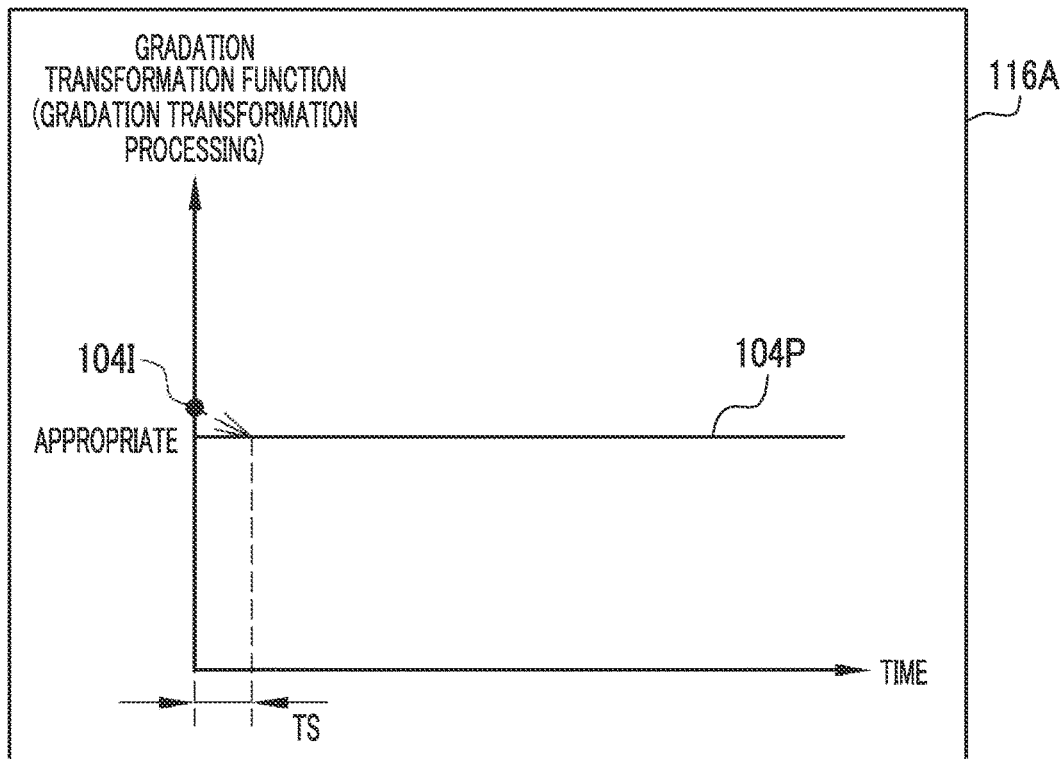
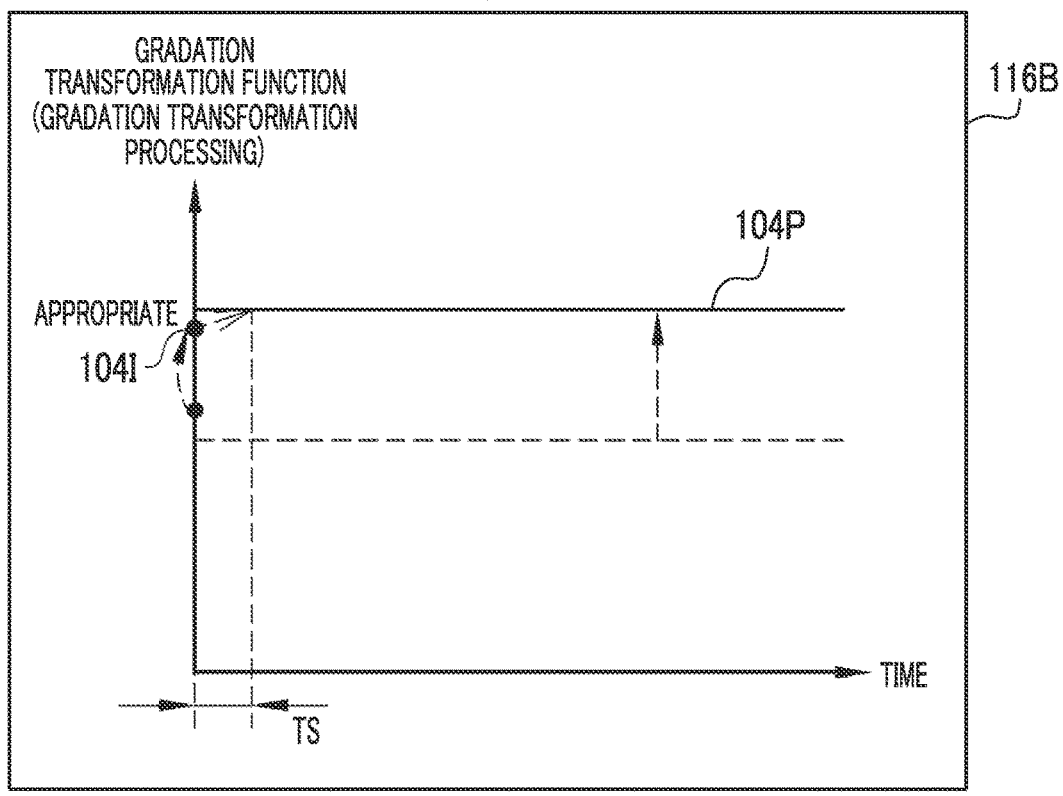

FIG. 24

PROCESSING APPARATUS, METHOD OF OPERATING PROCESSING APPARATUS, AND OPERATION PROGRAM FOR PROCESSING APPARATUS

CROSS-REFERENCE TO RELATED APPLICATIONS

The present application claims priority under 35 U.S.C. § 119 to Japanese Patent Application No. 2020-098879, filed on Jun. 5, 2020. The above application is hereby expressly incorporated by reference, in its entirety, into the present application.

BACKGROUND

1. Technical Field

A technique of the present disclosure relates to a processing apparatus, a method of operating a processing apparatus, and an operation program for a processing apparatus.

2. Description of the Related Art

In a medical field, for example, a radioscopy apparatus is used for various operations, such as a gastric barium test, cystography, and orthopedic reduction. The radioscopy apparatus continuously irradiates a subject with radiation in a comparatively low dose from a radiation source and displays radiographic images output from the radiation detector on a display in a form of video in real time.

In the radioscopy apparatus, suppressing fluctuation of contrast between frames of a radiographic image constituting video leads to improvement of diagnosability. For this reason, in the related art, for example, as described in JP2011-005050A, a method that appropriately controls a gradation transformation function (referred to as a tone curve) for use in gradation transformation processing of a radiographic image of a present frame based on a radiographic image of a previous frame to suppress fluctuation of contrast between the frames has been implemented.

SUMMARY

Radioscopy by the radioscopy apparatus is started, for example, in a case where an operator depresses a foot switch with a foot. In a first stage of radioscopy of which the start is instructed by the operator depressing the foot switch with the foot, there is of course no radiographic image of a previous frame to be referred, and thus, a default gradation transformation function is used for the gradation transformation processing. Then, the default gradation transformation function is changed by a radiographic image output one at a time through radioscopy, and finally, becomes an appropriate gradation transformation function corresponding to a body thickness of a subject.

Until the default gradation transformation function becomes the appropriate gradation transformation function, in other words, from when radioscopy is started until the gradation transformation processing becomes appropriate, video display of the radiographic image is not performed even though the operator depresses the foot switch with the foot and the irradiation of the radiation is performed. For this reason, the operator needs to wait for a start of an operation while the video display of the radiographic image is not performed. The foot switch is frequently operated to repeat irradiation and stop of radiation several times depending on the operation, and thus, such delay makes the operator feel stress. Accordingly, how to reduce the time needed from when radioscopy is started until the gradation transformation processing becomes appropriate is an extremely important issue for the radioscopy apparatus.

An object of the technique of the present disclosure is to provide a processing apparatus, a method of operating a processing apparatus, and an operation program for a processing apparatus capable of reducing a time needed from when radioscopy is started until gradation transformation processing becomes appropriate.

To achieve the above-described object, the present disclosure provides a processing apparatus that is used for a radioscopy apparatus including a radiation source configured to continuously irradiate a subject with radiation and a radiation detector configured to detect the radiation transmitted through the subject to output a radiographic image. The processing apparatus comprises at least one processor. The processor is configured to acquire a body thickness of the subject measured by a body thickness measurement sensor, set a gradation transformation function for use in gradation transformation processing to the radiographic image corresponding to the body thickness, acquire the radiographic image output from the radiation detector, and start the gradation transformation processing with the set gradation transformation function.

It is preferable that the processor is configured to, in the gradation transformation function, as the body thickness is thinner, increase a range of an output pixel value with respect to a range where an input pixel value is relatively high, more than a range of an output pixel value with respect to a range where an input pixel value is relatively low.

It is preferable that the processor is configured to, in the gradation transformation function, as the body thickness is thicker, increase a range of an output pixel value with respect to a range where an input pixel value is relatively low, more than a range of an output pixel value with respect to a range where an input pixel value is relatively high.

It is preferable that the processor is configured to correct a default gradation transformation function corresponding to the body thickness to generate gradation transformation function to be set.

It is preferable that the processor is configured to generate the gradation transformation function having an S-curved shape from the default gradation transformation function having a linear shape.

It is preferable that the processor is configured to make the body thickness measurement sensor measure the body thickness in a case where the irradiation of the radiation is not performed.

It is preferable that the processor is configured to make the body thickness measurement sensor measure the body thickness in synchronization with a timing at which the radiation detector outputs the radiographic image for offset correction.

It is preferable that the body thickness measurement sensor is a distance measurement camera that outputs a distance image representing a distance to a surface of an object using a time-of-flight system, and the processor is configured to convert the body thickness from the distance image.

The present disclosure provides a method of operating a processing apparatus that is used for a radioscopy apparatus including a radiation source configured to continuously irradiate a subject with radiation and a radiation detector configured to detect the radiation transmitted through the subject to output a radiographic image. A processor executes body thickness acquisition processing of acquiring a body thickness of the subject measured by a body thickness measurement sensor, setting processing of setting a gradation transformation function for use in gradation transformation processing to the radiographic image corresponding to the body thickness, image acquisition processing of acquiring the radiographic image output from the radiation detector, and image processing of starting the gradation transformation processing with the set gradation transformation function.

The present disclosure provides an operation program for a processing apparatus that is used for a radioscopy apparatus including a radiation source configured to continuously irradiate a subject with radiation and a radiation detector configured to detect the radiation transmitted through the subject to output a radiographic image. The operation program causes a processor to execute body thickness acquisition processing of acquiring a body thickness of the subject measured by a body thickness measurement sensor, setting processing of setting a gradation transformation function for use in gradation transformation processing to the radiographic image corresponding to the body thickness, image acquisition processing of acquiring the radiographic image output from the radiation detector, and image processing of starting the gradation transformation processing with the set gradation transformation function.

According to the technique of the present disclosure, it is possible to provide a processing apparatus, a method of operating a processing apparatus, and an operation program for a processing apparatus capable of reducing a time needed from when radioscopy is started until gradation transformation processing becomes appropriate.

BRIEF DESCRIPTION OF THE DRAWINGS

Exemplary embodiments according to the technique of the present disclosure will be described in detail based on the following figures, wherein:

FIG. 2 is a diagram showing a manner in which a radiation generation unit and a radiation detector reciprocate along a longitudinal direction of an imaging table;

FIGS. 3A and 3B are diagrams showing a manner in which an angle of the radiation generation unit is changed, FIG. 3A shows a manner in which the radiation generation unit is directed toward the left, and FIG. 3B shows a manner in which the radiation generation unit is directed toward the right;

FIG. 14 is a diagram showing a correction coefficient table;

FIG. 15 is a graph showing a default gradation transformation function;

FIG. 16 is a diagram showing processing of a setting unit in a case where the body thickness is comparatively thin;

FIG. 23 is a graph showing the outline of the gradation transformation processing according to the technique of the present disclosure in a case where the body thickness is changed during an operation;

FIG. 24 is a diagram showing a manner of tomosynthesis imaging;

DETAILED DESCRIPTION

First Embodiment

Figure 1:
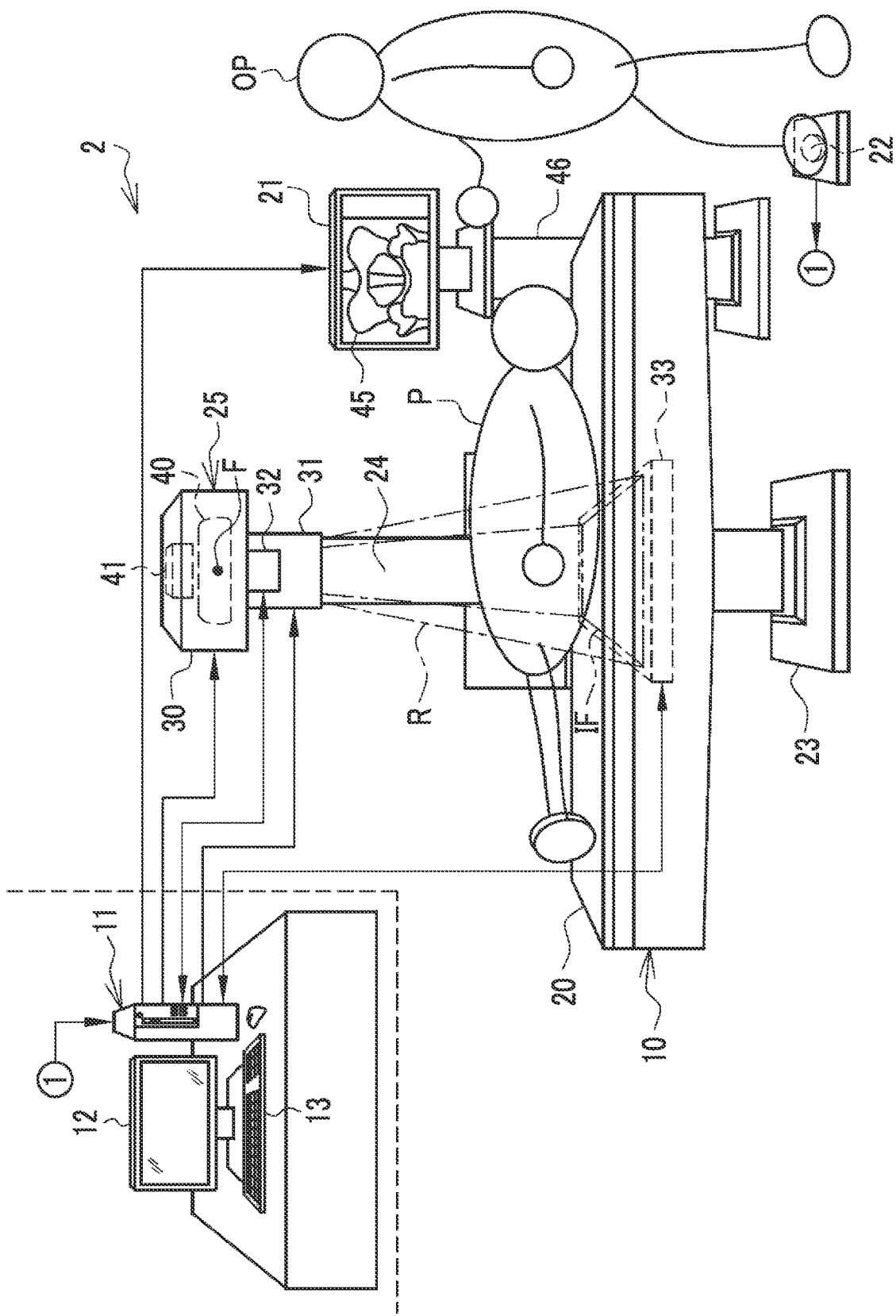
FIG. 1 is a diagram showing a radioscopy system.

In FIG. 1, a radioscopy system 2 comprises a radioscopy apparatus 10 and a console 11. The radioscopy apparatus 10 is provided in, for example, an operation room of a medical facility. The operation room is a room where an operator OP, such as a radiographer or a physician, performs an operation, such as a gastric barium test, cystography, or orthopedic reduction, to a patient P. The radioscopy apparatus 10 performs radioscopy to the patient P under operation. The patient P is an example of a "subject" according to the technique of the present disclosure.

The console 11 is an example of a "processing apparatus" according to the technique of the present disclosure, and is provided in, for example, a control room next to the operation room. The console 11 controls the operation of each unit of the radioscopy apparatus 10. The console 11 is, for example, a desktop personal computer, and has a display 12 and an input device 13, such as a keyboard or a mouse. The display 12 displays an imaging order or the like from a radiology information system (RIS). The input device 13 is operated by the operator OP in designating an imaging menu corresponding to the imaging order, or the like.

The radioscopy apparatus 10 has an imaging table 20, an operator monitor 21, a foot switch 22, and the like. The imaging table 20 is supported on a floor surface of the operation room by a stand 23. A radiation generation unit 25 is attached to the imaging table 20 through a post 24. The radiation generation unit 25 is constituted of a radiation source 30, a collimator 31, and a distance measurement camera 32. A radiation detector 33 is incorporated in the imaging table 20.

The radiation source 30 has a radiation tube 40. The radiation tube 40 emits radiation R, such as X-rays or y-rays, and irradiates the patient P lying on the imaging table 20 with the radiation R, for example. The radiation tube 40 is provided with a filament, a target, a grid electrode, and the like (all are not shown). A voltage is applied between the filament as a cathode and the target as an anode from a voltage generator 41. The voltage that is applied between the filament and the target is referred to as a tube voltage. The filament discharges thermoelectrons according to the applied tube voltage toward the target. The target radiates the radiation R with collision of the thermoelectrons from the filament. The grid electrode is disposed between the filament and the target. The grid electrode changes a flow rate of the thermoelectrons from the filament toward the target depending on the voltage applied from the voltage generator 41. The flow rate of the thermoelectrons from the filament toward the target is referred to as a tube current. The tube voltage and the tube current are set as irradiation conditions (see FIG. 8) along with an irradiation time.

The collimator 31 and the distance measurement camera 32 are attached to a lower portion of the radiation source 30. The collimator 31 limits an irradiation field IF of the radiation R generated from the radiation tube 40. For example, the collimator 31 has a configuration in which four shield plates formed of lead or the like shielding the radiation R are disposed on respective sides of a quadrangle, and an emission opening of the quadrangle transmitting the radiation R is formed in a center portion. The collimator 31 changes the positions of the shield plates to change an opening degree of the emission opening, and accordingly, changes the irradiation field IF.

The distance measurement camera 32 is a camera that measures a distance to object surface using a time-of-flight (TOF) system. The distance measurement camera 32 is an example of a "body thickness measurement sensor" according to the technique of the present disclosure. The distance measurement camera 32 is viewed to be substantially as the same position as the radiation source 30, more exactly, a focus F of the radiation tube 40 at which the radiation R is generated, as viewed from the patient P side. For this reason, the distance measurement camera 32 may measure a distance between the radiation source 30 and an object surface. The object surface may be, for example, a body surface of the patient P or a surface of the imaging table 20. A distance between the focus F and the distance measurement camera 32 may be measured in advance, and a result obtained by adding the distance measured in advance between the focus F and the distance measurement camera 32 to the distance measured by the distance measurement camera 32 may be set as the distance between the radiation source 30 and the object surface. In the example, the distance between the radiation source 30 and the surface of the imaging table 20 is invariable.

The radiation detector 33 has a configuration in which a plurality of pixels that are sensitive to the radiation R or visible light converted from the radiation R by a scintillator to generate signal charge are arranged. Such a radiation detector 33 is referred to as a flat panel detector (FPD). The radiation detector 33 detects the radiation R emitted from the radiation tube 40 and transmitted through the patient P, and outputs a radiographic image 45. The radiation detector 33 transmits the radiographic image 45 to the console 11. The radiographic image 45 is also referred to as a perspective image.

The operator monitor 21 is supported on the floor surface of the operation room by a stand 46. The radiographic image 45 that is output from the radiation detector 33 and is subjected to various kinds of image processing with the console 11 is displayed on the operator monitor 21 in a form of video in real time.

The foot switch 22 is a switch for the operator OP giving an instruction to start and end radioscopy while being seated in the operation room. In a case where the operator OP depresses the foot switch 22 with a foot, radioscopy is started. Then, while the operator OP is depressing the foot switch 22 with the foot, radioscopy is continued. In a case where the operator OP releases the foot from the foot switch 22, and the depression of the foot switch 22 is released, radioscopy ends.

In a case where the foot switch 22 is depressed with the foot of the operator OP, the filament of the radiation tube 40 is pre-heated, and simultaneously the rotation of the target is started. After the filament reaches a specified temperature, and the target is at a specified rotation speed, the tube voltage is applied from the voltage generator 41, and the radiation R is generated from the radiation tube 40.

As shown in FIG. 2, not only the post 24 but also the radiation generation unit 25 can reciprocate along a longitudinal direction of the imaging table 20 by a movement mechanism (not shown), such as a motor. The radiation detector 33 can also reciprocate along the longitudinal direction of the imaging table 20 in conjunction with the movement of the radiation generation unit 25. The radiation detector 33 is moved to a facing position where the center thereof coincides with the focus F of the radiation tube 40. The imaging table 20 is provided with a control panel (not shown) for inputting an instruction to move the radiation generation unit 25 and the radiation detector 33. The operator OP inputs an instruction through the control panel and moves the radiation generation unit 25 and the radiation detector 33 to desired positions. The radiation generation unit 25 and the radiation detector 33 can be controlled by remote control by a control console (not shown) from the control room.

As shown in FIGS. 3A and 3B, the radiation generation unit 25 can change an angle right and left with respect to the post 24 with a hand of the operator OP. A changeable maximum angle is, for example, 90° right and left. The changing of the angle of the radiation generation unit 25 with respect to the post 24 can be controlled by remote control from the control room.

Figure 4:
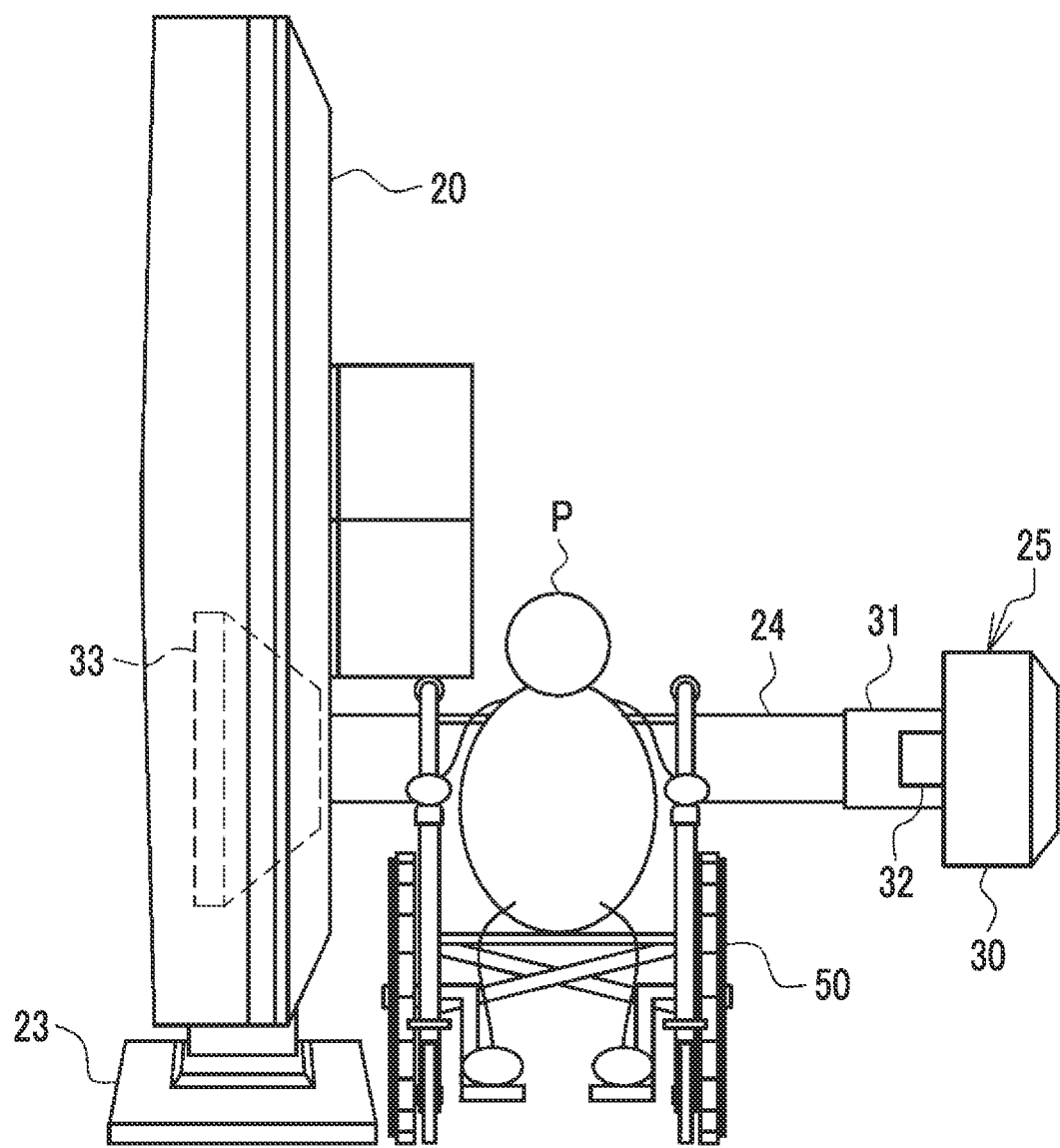
FIG. 4 is a diagram showing a manner in which radioscopy is performed on a patient in a wheelchair with an imaging table and a post in an upright state.
Figure 5:
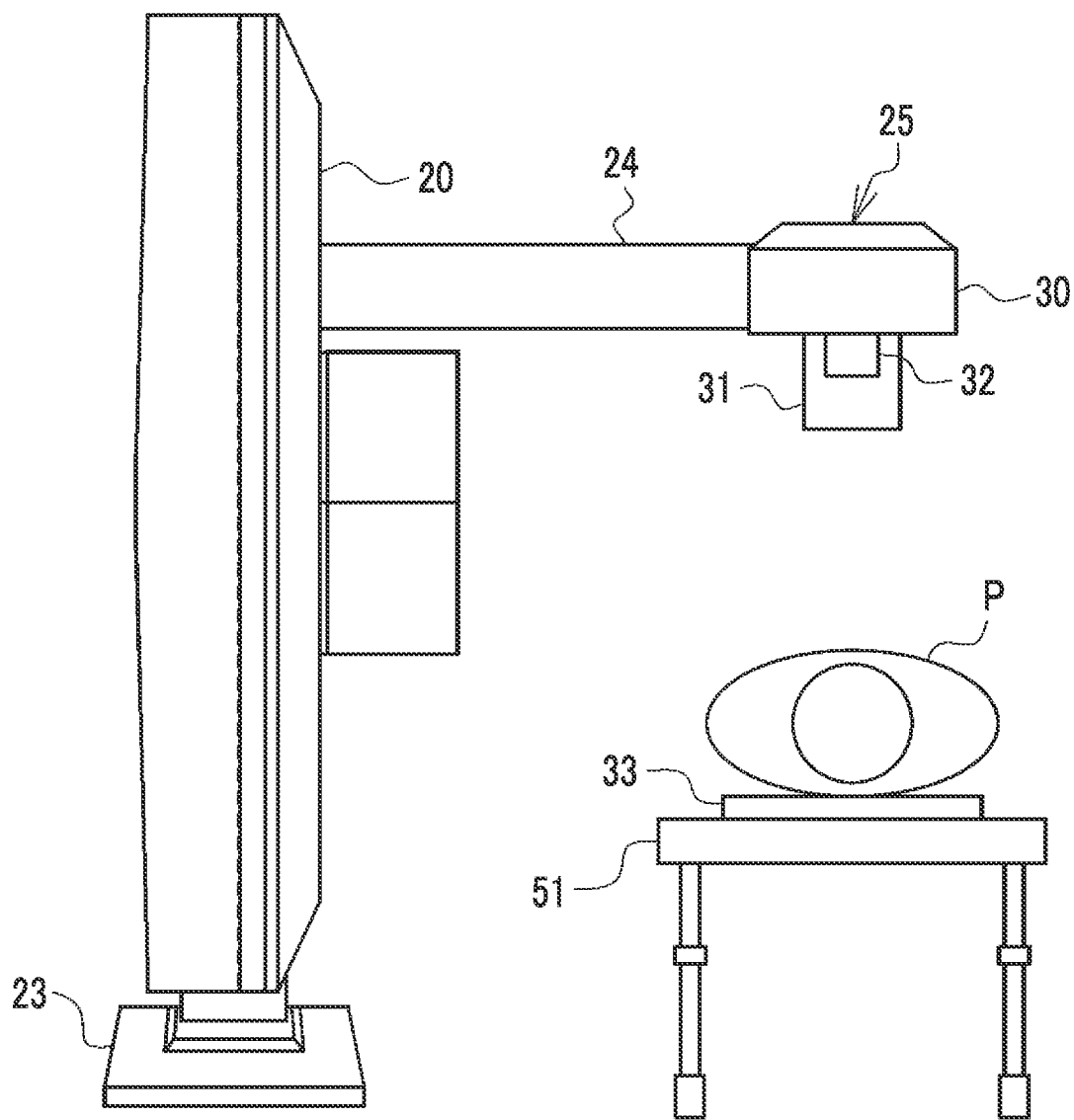
FIG. 5 is a diagram showing a manner in which radioscopy is performed on a patient on a stretcher with the imaging table and the post in the upright state.

The imaging table 20 and the post 24 can rotate between a decubitus state shown in FIGS. 1 and 2 and an upright state shown in FIGS. 4 and 5 by a rotation mechanism (not shown), such as a motor. The decubitus state is a state in which the surface of the imaging table 20 is parallel to the floor surface and the post 24 is perpendicular to the floor surface. On the contrary, the upright state is a state in which the surface of the imaging table 20 is perpendicular to the floor surface, and the post 24 is parallel to the floor surface.

In the upright state, not only radioscopy on the patient P in an upright posture, but also radioscopy on the patient P in a wheelchair 50 as shown in FIG. 4 can be performed. In the upright state, radioscopy on the patient P on a stretcher 51 as shown in FIG. 5 can also be performed. In the case of FIG. 5, the radiation detector 33 is detached from the imaging table 20 and is set between the patient P and the stretcher 51.

Figure 6:
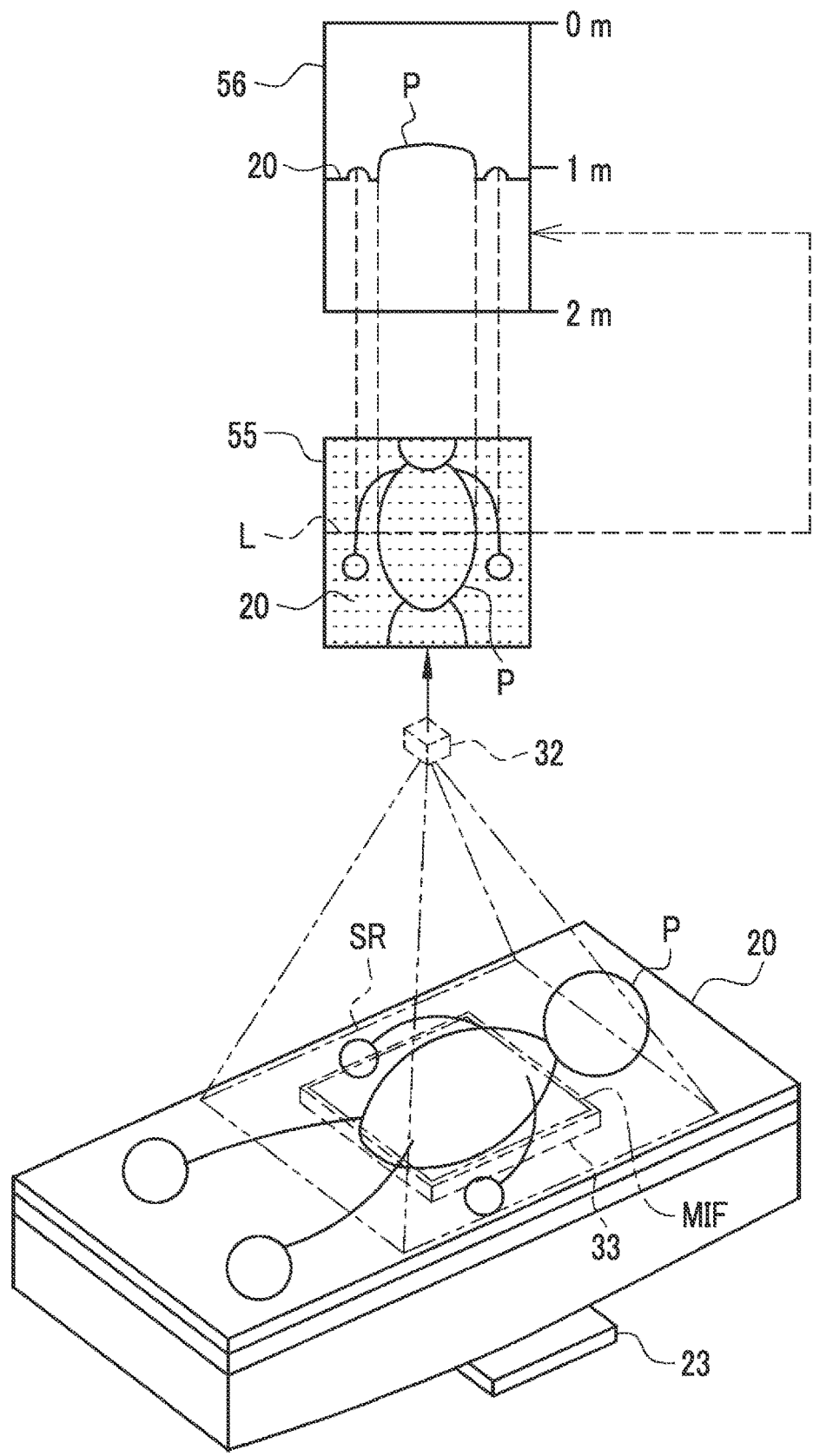
FIG. 6 is a diagram showing a manner in which the patient and the periphery of the patient are imaged with a distance measurement camera and a distance image representing a distance between a radiation source and an object surface is output.

As shown in FIG. 6, the distance measurement camera 32 images a rectangular imaging range SR including the patient P and the periphery of the patient P, and outputs a distance image 55. The imaging range SR is a range sufficiently wider than a maximum irradiation field MIF of the radiation R, and covers the entire maximum irradiation field MIF of the radiation R.

The distance image 55 is an image in which an attachment position of the distance measurement camera 32, that is, a position of the radiation source 30 is represented as 0 m, as illustrated with a profile 56 of a line L at the center. The distance image 55 has, as a pixel value of each pixel, a distance between the radiation source 30 and a surface of an object in the imaging range SR, such as the patient P or the imaging table 20.

Figure 7:
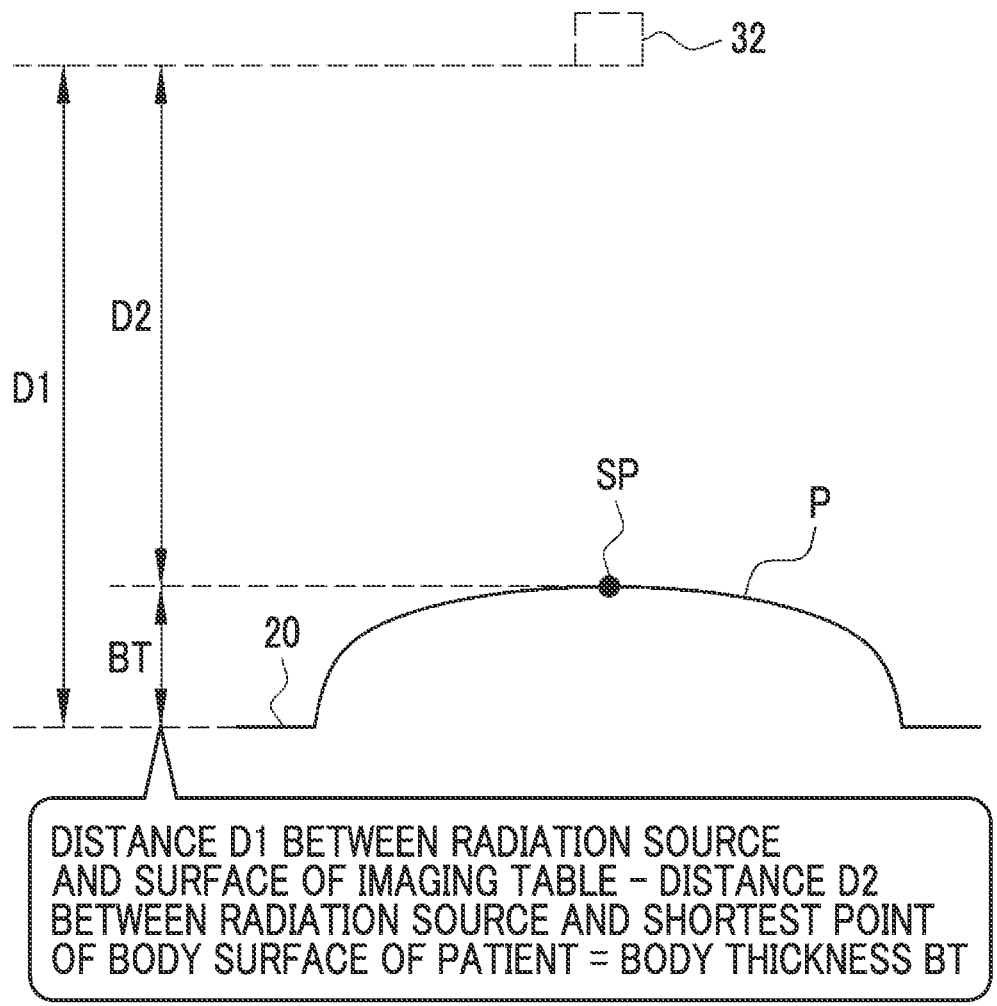
FIG. 7 is a diagram showing a manner in which a body thickness of the patient is calculated based on a distance between the radiation source and a surface of the imaging table and a distance between the radiation source and a shortest point of a body surface of the patient.

As shown in FIG. 7, in a case where the distance radiation source 30 (distance measurement camera 32) and the surface of the imaging table 20 is D1, and the distance between the radiation source 30 (distance measurement camera 32) and a shortest point SP of a body surface of the patient P is D2, a body thickness BT of the patient P can be calculated by Expression (1) described below.

$$BT = D1 - D2 \quad (1)$$

As described above, the distance D1 between the radiation source 30 and the surface of the imaging table 20 is invariable. For this reason, in a case where the distance D2 between the radiation source 30 and the shortest point SP of the body surface of the patient P is derived from the distance image 55, the body thickness BT is simply calculated. In the case of FIG. 5 where radioscopy is performed on the patient P on the stretcher 51, the body thickness BT is calculated by further subtracting a thickness of the radiation detector 33.

The distance D2 is derived as follows, for example. First, the distance D1 is invariable and known, and thus, a region of the distance image 55 having a distance less than the distance D1 as a pixel value is recognized as a region of the patient P. Next, a position at the shortest distance in the recognized region of the patient P, that is, the shortest point SP is searched, and a pixel value of the searched shortest point SP is derived as the distance D2. As in the example, in a case where the distance D1 between the radiation source 30 and the surface of the imaging table 20 is invariable, the distance D2 between the radiation source 30 and the shortest point SP of the body surface of the patient P may be regarded as the body thickness BT.

Figure 8:
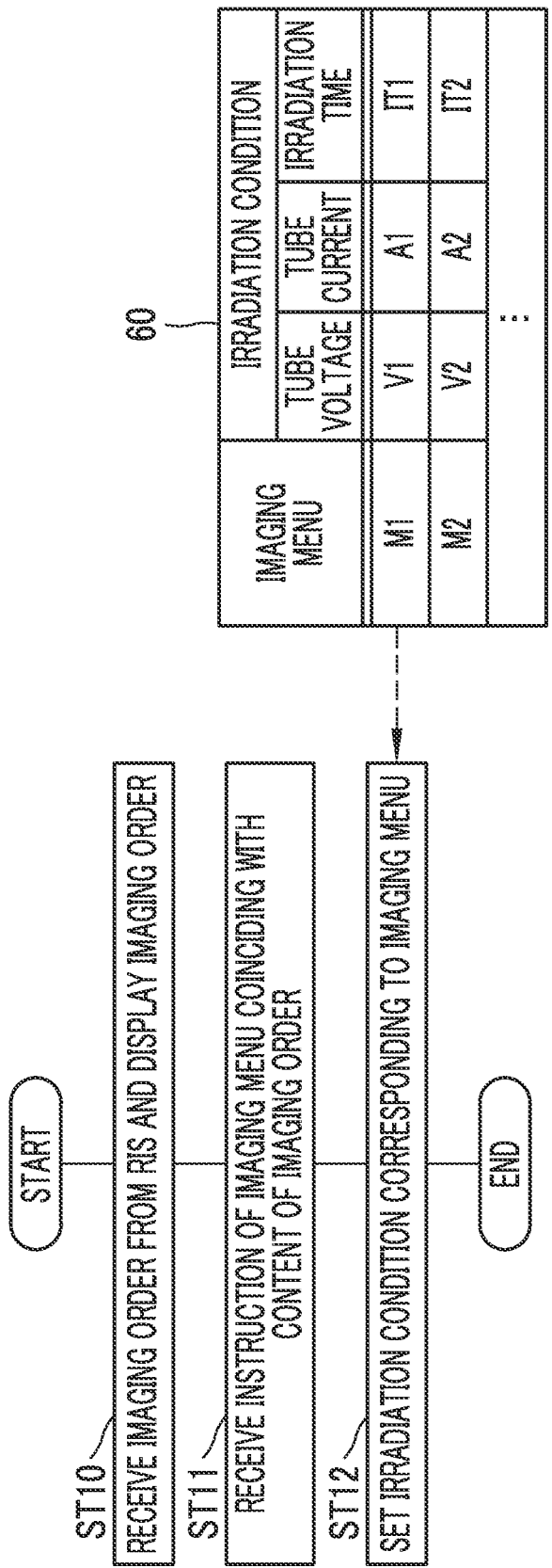
FIG. 8 is a flowchart showing a procedure for setting irradiation conditions.

As shown in FIG. 8, prior to radioscopy, the console 11 receives the imaging order from the RIS and displays the imaging order on the display 12 (Step ST10). In the imaging order, patient identification data (ID) for identifying the patient P, an instruction of an operation by a physician of a treatment department who issues the imaging order, and the like are registered. The operator OP confirms the content of the imaging order through the display 12.

The console 11 displays a plurality of kinds of imaging menus prepared in advance on the display 12 in an alternatively selectable form. The operator OP selects one imaging menu coinciding with the content of the imaging order through the input device 13. With this, the console 11 receives an instruction of the imaging menu (Step ST11).

The console 11 sets irradiation conditions corresponding to the instructed imaging menu with reference to an irradiation condition table 60 (Step ST12). After selecting the imaging menu, the operator OP performs positioning and the like of the radiation source 30, the radiation detector 33, and the patient P, and depresses the foot switch 22 with the foot to start radioscopy. The irradiation conditions have content where the irradiation of the radiation R is performed with an extremely low dose compared to a case where general radiography is performed.

Figure 9:
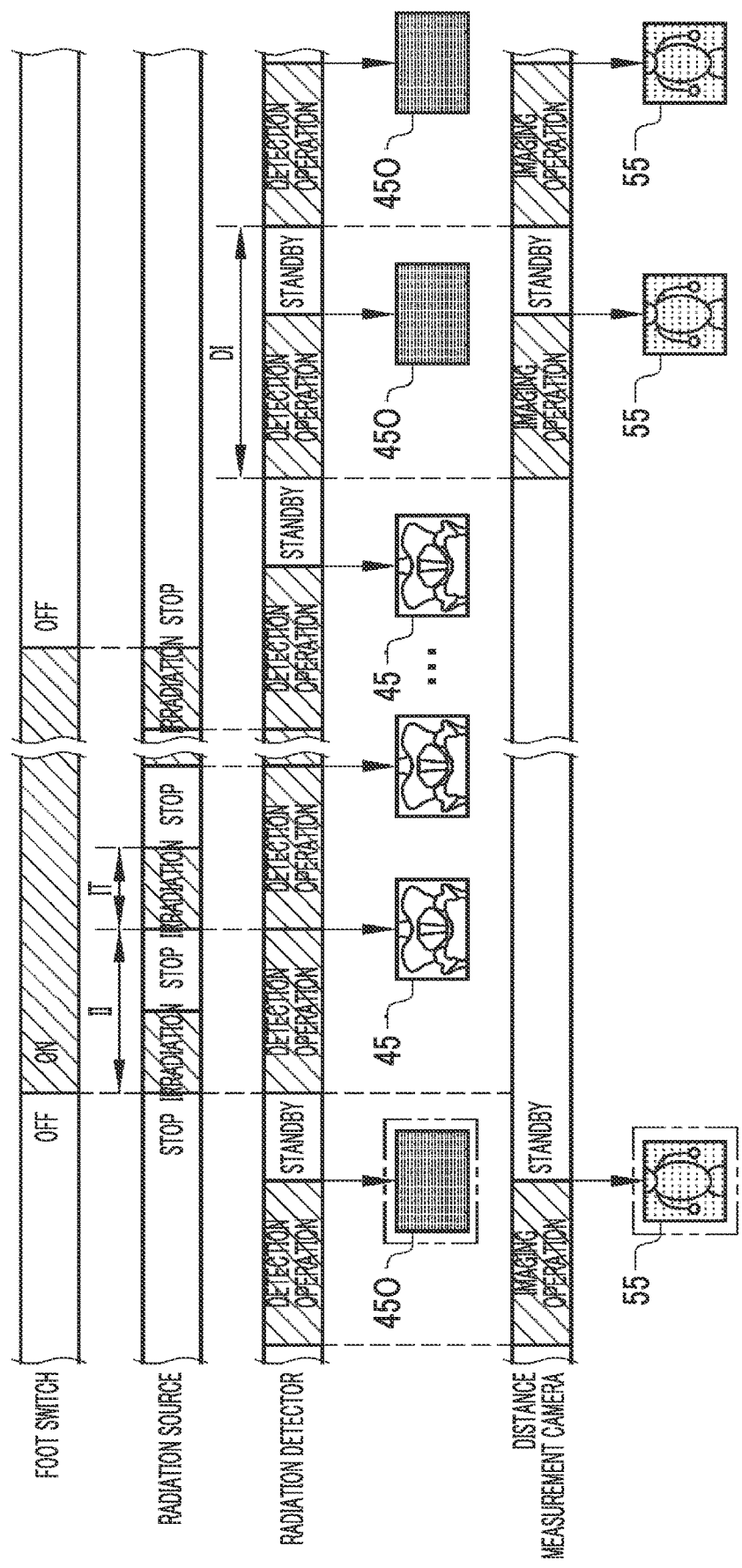
FIG. 9 is a timing chart showing an operation timing of each unit in radioscopy.

As shown in FIG. 9, the radiation source 30 starts the irradiation of the radiation R set under the irradiation conditions in synchronization with a timing at which the foot switch 22 is depressed with the foot of the operator OP, that is, a timing from off to on in the drawing. The radiation source 30 repeats the irradiation and the stop of the radiation R at an irradiation interval II set in advance while the foot switch 22 is being depressed with the foot of the operator OP. That is, the radiation source 30 continuously irradiates the patient P with the radiation R. The radiation source 30 stops the irradiation of the radiation R in a case where the depression of the foot switch 22 is released. The irradiation interval II is variable with, for example, about 0.033 seconds (30 frames per second (fps) as converted into a frame rate) as an upper limit. A sign IT indicates an irradiation time set under the irradiation conditions.

The radiation detector 33 starts a detection operation in synchronization with an irradiation start timing of the radiation R. The radiation detector 33 repeats the detection operation while the foot switch 22 is being depressed with the foot of the operator OP, and the irradiation of the radiation R is being performed from the radiation source 30 in a pulsed manner. With the repetitive detection operations during the irradiation of the radiation R, the radiation detector 33 outputs the radiographic image 45 at the irradiation interval II.

The radiation detector 33 performs the detection operation even though the depression of the foot switch 22 is released, and the irradiation of the radiation R is not performed from the radiation source 30. The radiation detector 33 repeatedly performs the detection operation in a state in which the irradiation of the radiation R is not performed, at a detection interval DI set in advance. The detection interval DI is a time sufficiently longer than the irradiation interval II of the radiation R, and is, for example, one minute. With the detection operation in a state in which the irradiation of the radiation R is not performed, the radiation detector 33 outputs a radiographic image for offset correction (hereinafter, referred to as an offset correction image) 45O. The radiation detector 33 transmits the offset correction image 45O to the console 11.

The distance measurement camera 32 performs an imaging operation of the distance image 55 in synchronization with a detection operation of the offset correction image 45O of the radiation detector 33. In other words, the distance measurement camera 32 measures the body thickness of the patient P in synchronization with a timing at which the radiation detector 33 outputs the offset correction image 45O.

In FIG. 9, although an aspect where the irradiation of the radiation R is performed in a pulsed manner has been exemplified, the present disclosure is not limited thereto. An aspect where the irradiation of the radiation R is consecutively performed while the foot switch 22 is being depressed with the foot of the operator OP may be employed. Even in an aspect where the irradiation of the radiation R is performed in a pulsed manner or an aspect where the irradiation of the radiation R is consecutively performed, the fact remains that the patient P is continuously irradiated with the radiation R.

Figure 10:
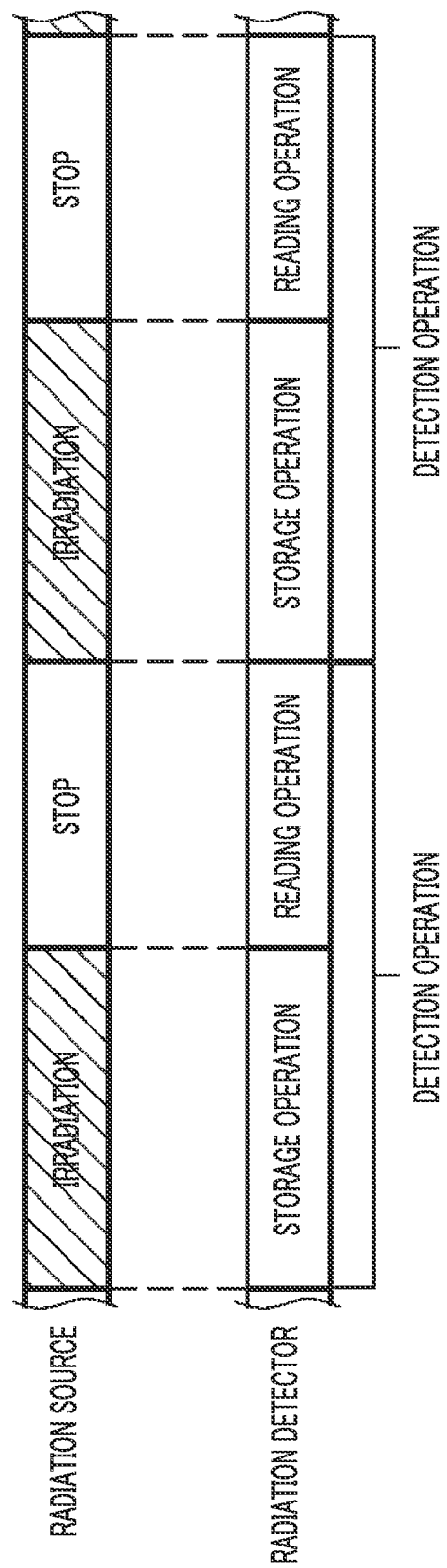
FIG. 10 is a timing chart showing specific content of a detection operation.

As shown in FIG. 10, the detection operation is constituted of a storage operation and a reading operation. The storage operation is an operation to store signal charge in a pixel, and is started in synchronization with the irradiation start timing of the radiation R. The reading operation is an operation to read the signal charge stored in the pixel and to output the signal charge as the radiographic image 45, and is started in synchronization with an irradiation end timing of the radiation R.

Figure 11:
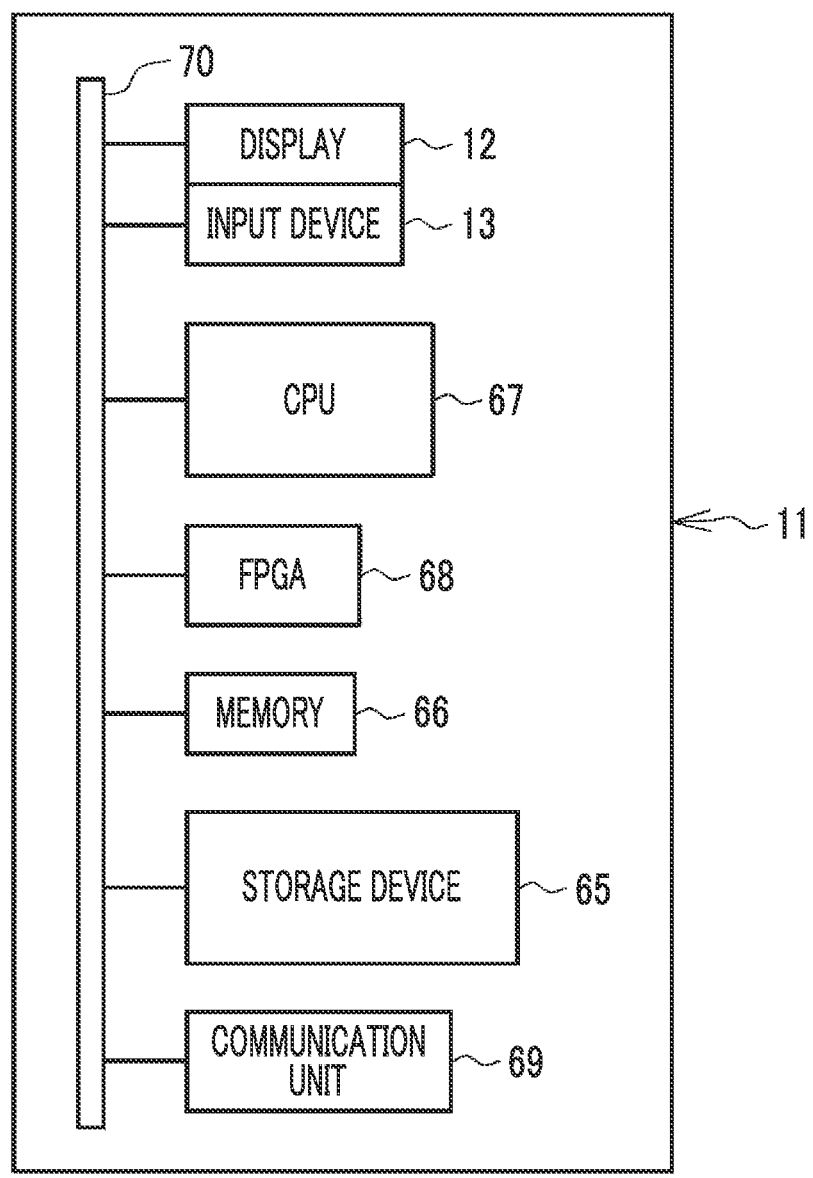
FIG. 11 is a block diagram of a computer constituting a console.

In FIG. 11, the computer constituting the console 11 comprises a storage device 65, a memory 66, a central processing unit (CPU) 67, a field programmable gate array (FPGA) 68, and a communication unit 69, in addition to the display 12 and the input device 13. Such devices and units are connected to one another through a busline 70.

The storage device 65 is a hard disk drive that is incorporated in the computer constituting the console 11 or a connected to the computer through a cable and a network. Alternatively, the storage device 65 is a disk array in which a plurality of hard disk drives are mounted. In the storage device 65, a control program, such as an operating system, various application programs, various kinds of data associated with such programs, and the like are stored. A solid state drive may be used instead of the hard disk drive.

The memory 66 is a work memory on which the CPU 67 executes processing. The CPU 67 loads a program stored in the storage device 65 to the memory 66 to execute processing compliant with the program. With this, the CPU 67 integrally controls the operation of each unit of the radioscopy apparatus 10. The communication unit 69 takes charge of communication of various kinds of information with each unit of the radioscopy apparatus 10.

Figure 12:
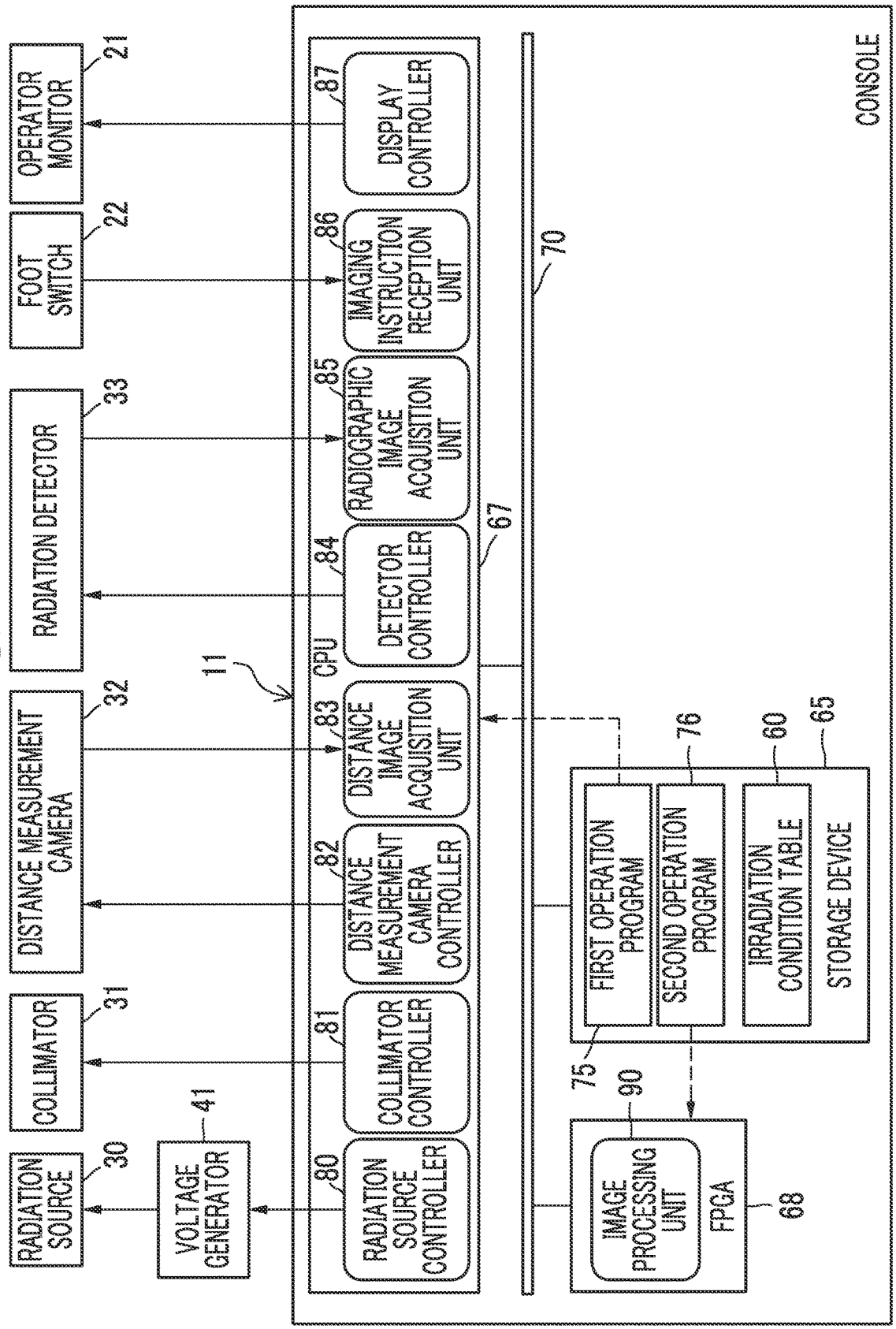
FIG. 12 is a block diagram showing functions of a CPU and an FPGA of the console.

In FIG. 12, in the storage device 65 of the console 11, a first operation program 75 and a second operation program 76 are stored. The first operation program 75 and the second operation program 76 are an application program that causes the computer constituting the console 11 to function as a "processing apparatus" according to the technique of the present disclosure. That is, the first operation program 75 and the second operation program 76 are an example of an "operation program for a processing apparatus" according to the technique of the present disclosure. In the storage device 65, the irradiation condition table 60 is also stored.

In a case where the first operation program 75 is activated, the CPU 67 of the computer constituting the console 11 functions as a radiation source controller 80, a collimator controller 81, a distance measurement camera controller 82, a distance image acquisition unit 83, a detector controller 84, a radiographic image acquisition unit 85, an imaging instruction reception unit 86, and a display controller 87 in cooperation with the memory 66 and the like. In a case where the second operation program 76 is activated, the FPGA 68 of the computer constituting the console 11 functions as an image processing unit 90. The CPU 67 and the FPGA 68 are an example of a "processor" according to the technique of the present disclosure.

The radiation source controller 80 controls the operation of the radiation source 30 to control the irradiation of the radiation R. The radiation source controller 80 reads the irradiation conditions corresponding to the imaging menu selected by the operator OP from the irradiation condition table 60 and sets the read irradiation condition in the voltage generator 41. The radiation source controller 80 causes the irradiation of the radiation R from the radiation source 30 through the voltage generator 41 under the set irradiation conditions. The radiation source controller 80 outputs irradiation start and stop timings of the radiation R to the detector controller 84.

The radiation source controller 80 performs auto brightness control (ABC). As known in the art, the ABC is feedback control where, to maintain the brightness of the radiographic image 45 within a given range, during radioscopy, the tube voltage, the tube current, an irradiation time IT, the irradiation interval II, and the like given to the radiation tube 40 are finely adjusted based on a brightness value (for example, an average value of brightness values of a center region of the radiographic image 45) of the radiographic image 45 sequentially output from the radiation detector 33. With the ABC, the brightness of the radiographic image 45 is prevented from being extremely changed due to body movement or the like of the patient P or the radiographic image 45 is prevented from being hardly observed.

The collimator controller 81 controls the operation of the shield plates of the collimator 31 and adjusts the opening degree of the emission opening formed by the shield plates to an opening degree corresponding to the imaging menu selected by the operator OP. The opening degree of the emission opening can also be adjusted by the operator OP through a control panel (not shown) provided in the collimator 31 itself.

The distance measurement camera controller 82 controls the operation of the distance measurement camera 32. Specifically, the distance measurement camera controller 82 makes the distance measurement camera 32 perform an imaging operation of the distance image 55 in synchronization with the timing at which the radiation detector 33 outputs the offset correction image 45O in a case where the irradiation of the radiation R is not performed.

The distance image acquisition unit 83 acquires the distance image 55 from the distance measurement camera 32. The distance image acquisition unit 83 outputs the distance image 55 to the image processing unit 90.

The detector controller 84 controls the operation of the radiation detector 33. The detector controller 84 makes the radiation detector 33 perform the storage operation in a case where the irradiation of the radiation R is started in radioscopy. The detector controller 84 makes the radiation detector 33 perform the reading operation in a case where the irradiation of the radiation R is stopped in radioscopy. With this, the radiographic image 45 is output from the radiation detector 33.

The detector controller 84 makes the radiation detector 33 perform the detection operation at the detection interval DI in a case where the irradiation of the radiation R is not performed. With this, the offset correction image 45O is output from the radiation detector 33.

The radiographic image acquisition unit 85 acquires the radiographic image 45 and the offset correction image 45O from the radiation detector 33. That is, the radiographic image acquisition unit 85 takes charge of "image acquisition processing" according to the technique of the present disclosure. The radiographic image acquisition unit 85 outputs the radiographic image 45 and the offset correction image 45O to the image processing unit 90.

The imaging instruction reception unit 86 receives an instruction to start and end radioscopy through the foot switch 22. The imaging instruction reception unit 86 outputs the received instruction to the radiation source controller 80 and the detector controller 84.

The display controller 87 performs control for displaying the radiographic image 45 subjected to various kinds of image processing with the image processing unit 90 on the operator monitor 21. The display controller 87 also performs control for displaying the imaging order, the imaging menu, and the like on the display 12.

The image processing unit 90 executes various kinds of image processing on the radiographic image 45. For example, the image processing unit 90 executes offset correction processing, sensitivity correction processing, defective pixel correction processing, and the like as the image processing.

The offset correction processing is processing for subtracting the offset correction image 45O output in a state in which the irradiation of the radiation R is not performed, from the radiographic image 45 output by radioscopy in units of pixels. In the offset correction processing, the latest offset correction image 45O most recently acquired by the radiographic image acquisition unit 85 and surrounded by a frame of a two-dot chain line in FIG. 9 is used. The image processing unit 90 executes the offset correction processing to remove fixed pattern noise due to dark charge or the like from the radiographic image 45.

The sensitivity correction processing is processing for correcting variation in sensitivity of each pixel of the radiation detector 33, variation or the like in output characteristic of a circuit that reads the signal charge, and the like based on sensitivity correction data. The defective pixel correction processing is processing of linearly interpolating a pixel value of a defective pixel with a pixel value of a surrounding normal pixel based on information of a defective pixel having an abnormal pixel value generated during shipment, during a periodic inspection, or the like.

The image processing unit 90 executes noise reduction processing, such as recursive filter processing or spatial filter processing, to the radiographic image 45 subjected to, for example, the offset correction processing, the sensitivity correction processing, and the defective pixel correction processing described above. The recursive filter processing is processing of adding the radiographic image 45 output further in the past than the radiographic image 45 to be processed to the radiographic image 45 to be processed and outputting a result of addition. The past radiographic image 45 is multiplied by an appropriate weighting coefficient before addition to the radiographic image 45 to be processed. Examples of the spatial filter processing include median filter processing using a median filter and Gaussian filter processing using a Gaussian filter. The image processing unit 90 outputs the radiographic image 45 subjected to various kinds of image processing to the display controller 87.

Figure 13:
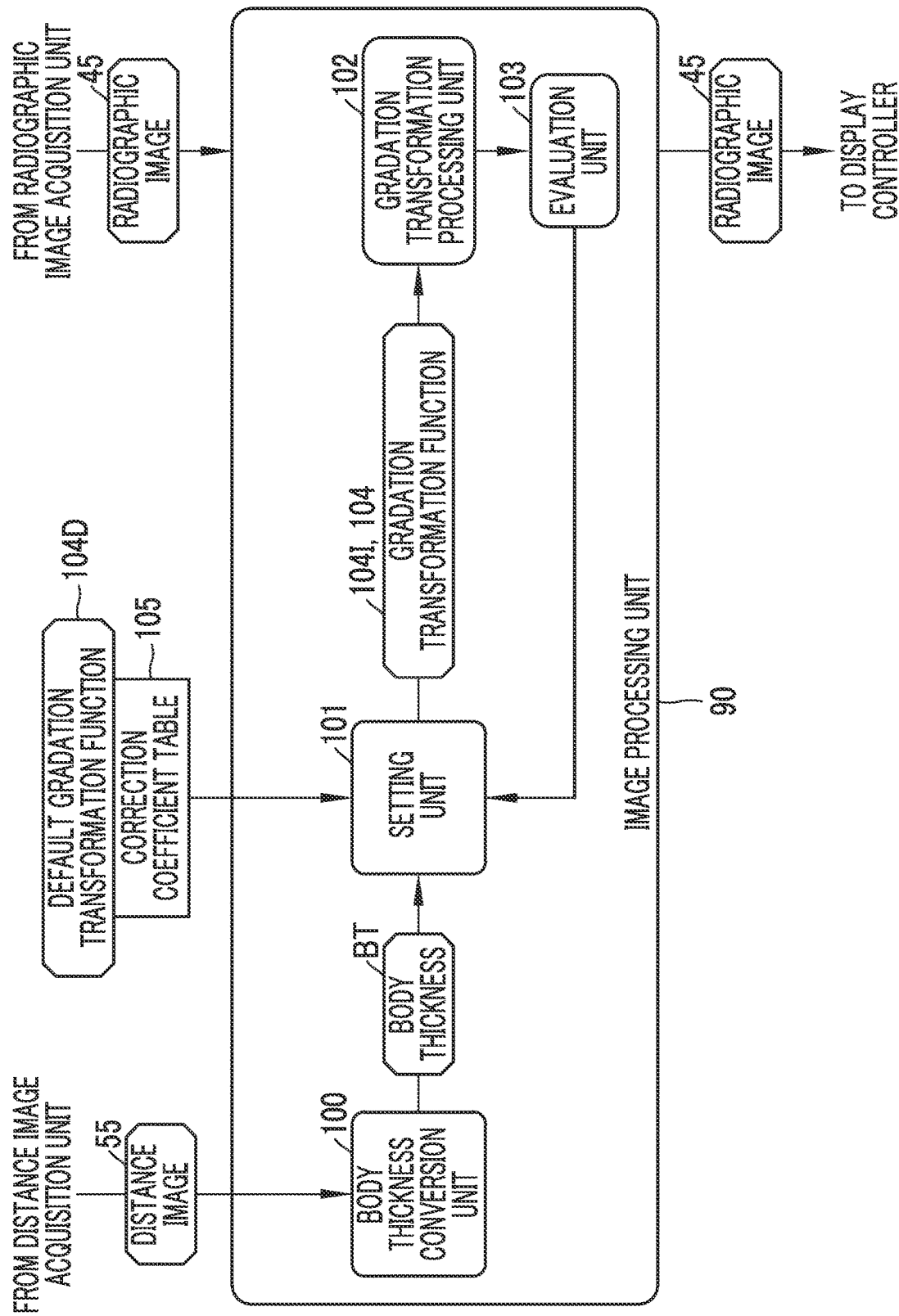
FIG. 13 is a block diagram showing details of an image processing unit.

As shown in FIG. 13, the image processing unit 90 has a body thickness conversion unit 100, a setting unit 101, a gradation transformation processing unit 102, and an evaluation unit 103, in addition to the respective units (not shown) that execute various kinds of processing.

The distance image 55 is input to the body thickness conversion unit 100 from the distance image acquisition unit 83. As shown in FIG. 7 and Expression (1), the body thickness conversion unit 100 subtracts the distance D2 between the radiation source 30 and the shortest point SP of the body surface of the patient P from the distance D1 between the radiation source 30 and the surface of the imaging table 20 to calculate the body thickness BT of the patient P. That is, the body thickness conversion unit 100 takes charge of "body thickness acquisition processing" according to the technique of the present disclosure. The body thickness conversion unit 100 outputs the calculated body thickness BT to the setting unit 101.

The setting unit 101 sets a gradation transformation function 104I for use first in the gradation transformation processing unit 102 from a default gradation transformation function 104D corresponding to the body thickness BT converted by the body thickness conversion unit 100 based on a distance image 55 acquired immediately before radioscopy is started and surrounded by a frame of a two-dot chain line in FIG. 9. That is, the setting unit 101 takes charge of "setting processing" according to the technique of the present disclosure.

The setting unit 101 refers to a correction coefficient table 105 in setting the gradation transformation function 104I. The correction coefficient table 105 is stored in the storage device 65. As shown in FIG. 14, a correction coefficient α corresponding to the body thickness BT is registered in the correction coefficient table 105. The setting unit 101 corrects the default gradation transformation function 104D by the correction coefficient α to generate the gradation transformation function 104I. The setting unit 101 outputs the set gradation transformation function 104I to the gradation transformation processing unit 102.

The gradation transformation processing unit 102 executes gradation transformation processing on the radiographic image 45 of a first frame with the gradation transformation function 104I set by the setting unit 101. That is, the gradation transformation processing unit 102 takes charge of "image processing" according to the technique of the present disclosure. The gradation transformation processing unit 102 outputs the radiographic image 45 subjected to the gradation transformation processing to the evaluation unit 103. The radiographic image 45 subjected to, for example, the offset correction processing, the sensitivity correction processing, and the defective pixel correction processing described above and before being subjected to the above-described noise reduction processing is input to the gradation transformation processing unit 102.

The evaluation unit 103 evaluates whether or not the gradation transformation processing by the gradation transformation processing unit 102 is appropriate (whether or not the gradation transformation function 104 is appropriate). The evaluation unit 103 derives, for example, a spatial frequency-strength characteristic of the radiographic image 45 after the gradation transformation processing. Then, the evaluation unit 103 evaluates that the gradation transformation processing is appropriate in a case where a peak of the strength is equal to or greater than a threshold frequency set in advance, and evaluates that the gradation transformation processing is not appropriate in a case where the peak of the strength is less than the threshold frequency. The evaluation unit 103 outputs an evaluation result to the setting unit 101.

In a case where the evaluation result from the evaluation unit 103 has the content that the gradation transformation processing is appropriate, the setting unit 101 outputs the gradation transformation function 104 set to the radiographic image 45 of a previous frame to the gradation transformation processing unit 102 as it is. In contrast, in a case where the evaluation result from the evaluation unit 103 has the content that the gradation transformation processing is not appropriate, the setting unit 101 resets the gradation transformation function 104 set to the radiographic image 45 of the previous frame and outputs the reset gradation transformation function 104 to the gradation transformation processing unit 102. The setting unit 101 repeatedly performs the resetting of the gradation transformation function 104 until the evaluation result from the evaluation unit 103 has the content that the gradation transformation processing is appropriate.

The image processing unit 90 does not output the radiographic image 45 after the gradation transformation processing to the display controller 87 until the evaluation unit 103 evaluates that the gradation transformation processing is appropriate. For this reason, the display controller 87 does not display the radiographic image 45 on the operator monitor 21 in a form of video until the gradation transformation processing becomes appropriate. In other words, the display controller 87 starts video display of the radiographic image 45 on the operator monitor 21 in a case where the gradation transformation processing becomes appropriate.

As shown in FIG. 15, the default gradation transformation function 104D has a linear shape where an input pixel value and an output pixel value are in a one-to-one basis relationship.

Figure 17:
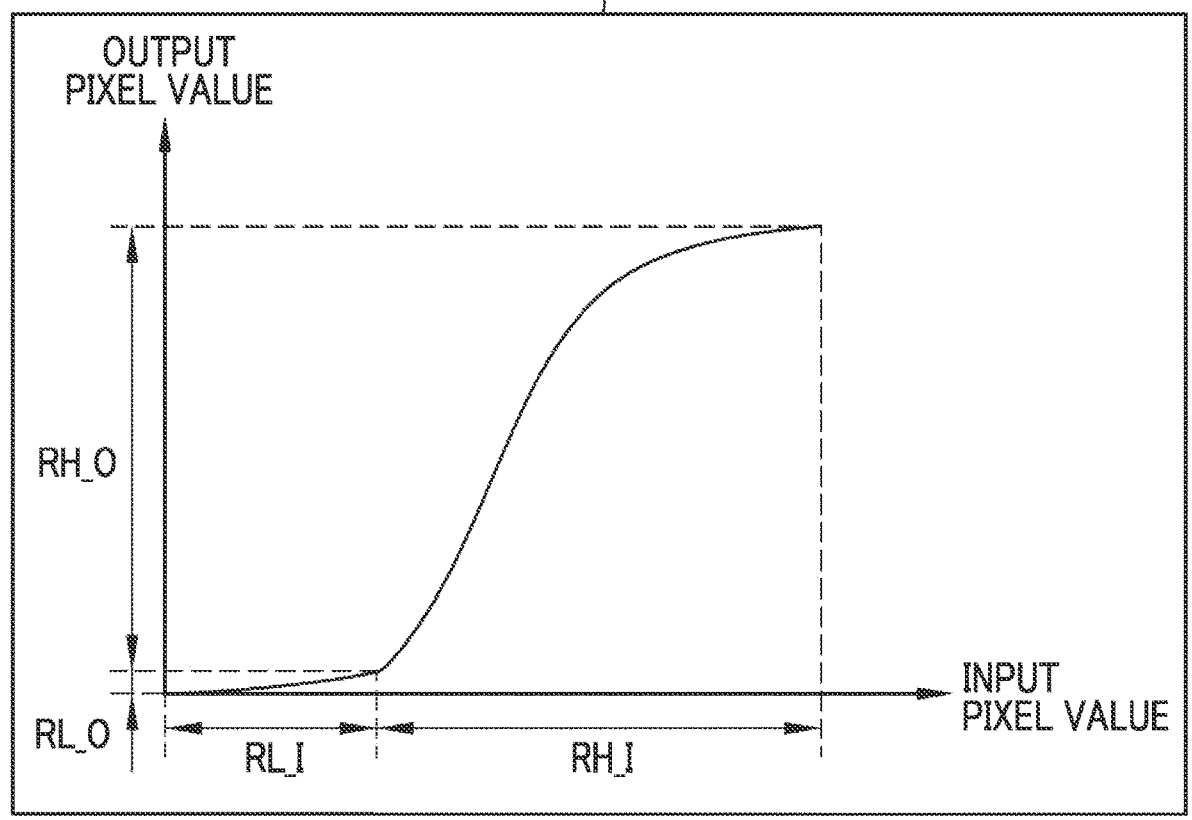
FIG. 17 is a graph showing a gradation transformation function that is set first in a case where the body thickness is comparatively thin.

As shown in FIGS. 16 and 17, in a case where the body thickness BT is comparatively thin, the setting unit 101 generates the gradation transformation function 104I having a characteristic that a range RH_O of an output pixel value with respect to a range RH_I where an input pixel value is relatively high increases more than a range RL_O of an output pixel value with respect to a range RL_I where an input pixel value is relatively low, from the default gradation transformation function 104D based on the correction coefficient α. With the gradation transformation function 104I having such a characteristic, as shown in FIG. 16 in comparison with a representative histogram 110A of the radiographic image 45 in a case where the body thickness BT is comparatively thin, contrast of a range R_ROI of a pixel value considered to represent an internal structure of the body of the patient P having a relatively high pixel value increases in the radiographic image 45.

Figure 18:
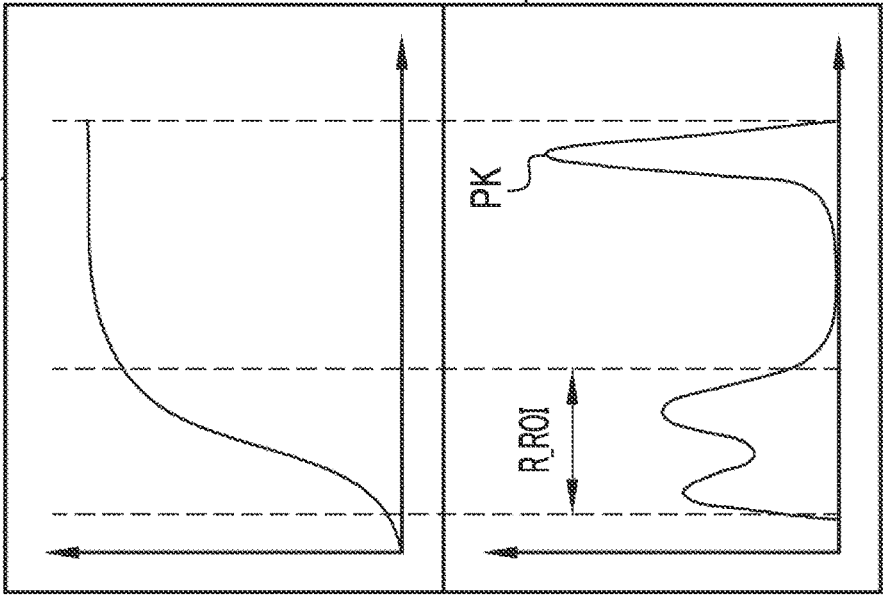
FIG. 18 is a diagram showing processing of the setting unit in a case where the body thickness is comparatively thick.
Figure 19:
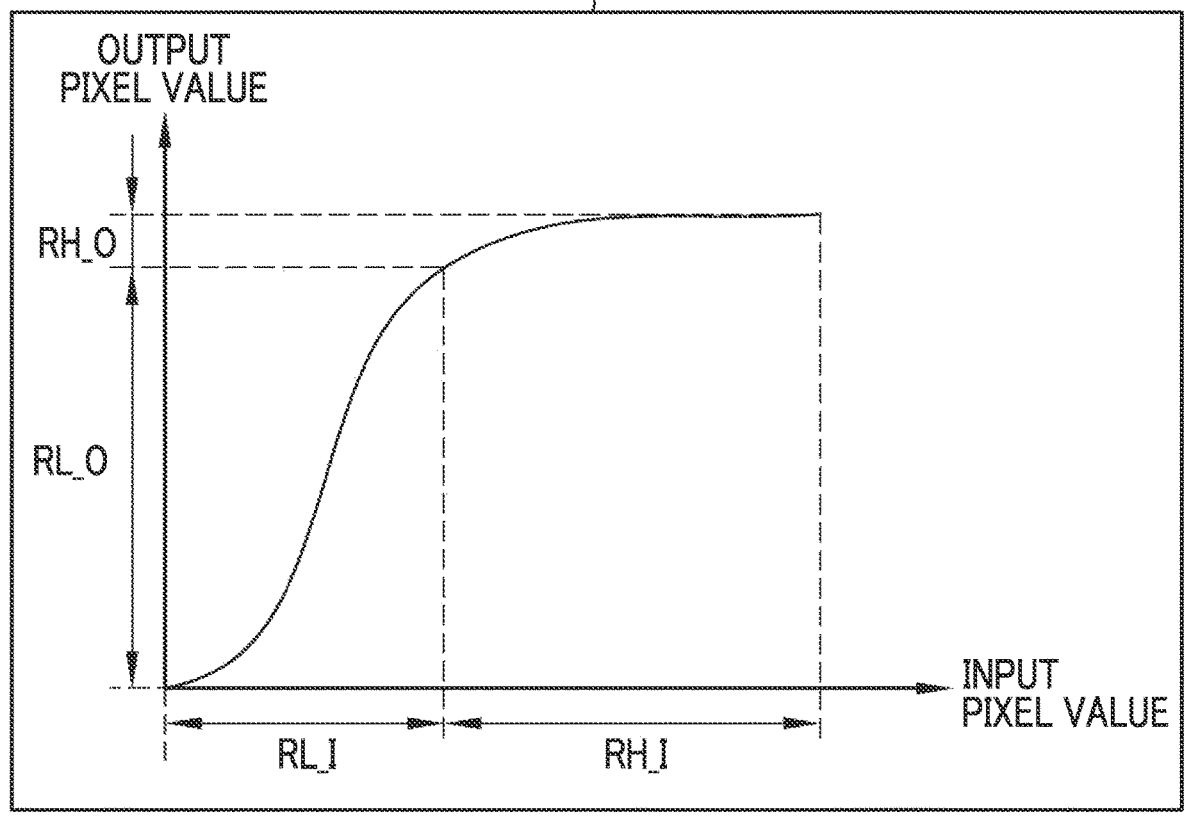
FIG. 19 is a graph showing a gradation transformation function that is set first in a case where the body thickness is comparatively thick.

In contrast, as shown in FIGS. 18 and 19, in a case where the body thickness BT is comparatively thick, the setting unit 101 generates the gradation transformation function 104I having a characteristic that a range RL_O of an output pixel value with respect to a range RL_I where an input pixel value is relatively low increases more than a range RH_O of an output pixel value with respect to a range RH_I where an input pixel value is relatively high, from the default gradation transformation function 104D based on the correction coefficient α. With the gradation transformation function 104I having such a characteristic, as shown in FIG. 18 in comparison with a representative histogram 110B of the radiographic image 45 in a case where the body thickness BT is comparatively thick, contrast of a range R_ROI of a pixel value considered to represent an internal structure of the body of the patient P having a relatively low pixel value increases in the radiographic image 45. A peak indicated by reference sign PK in FIGS. 16 and 18 represents a region of the radiation R that reaches the radiation detector 33 without being transmitted through the patient P, that is, a directly irradiated region.

Figure 20:
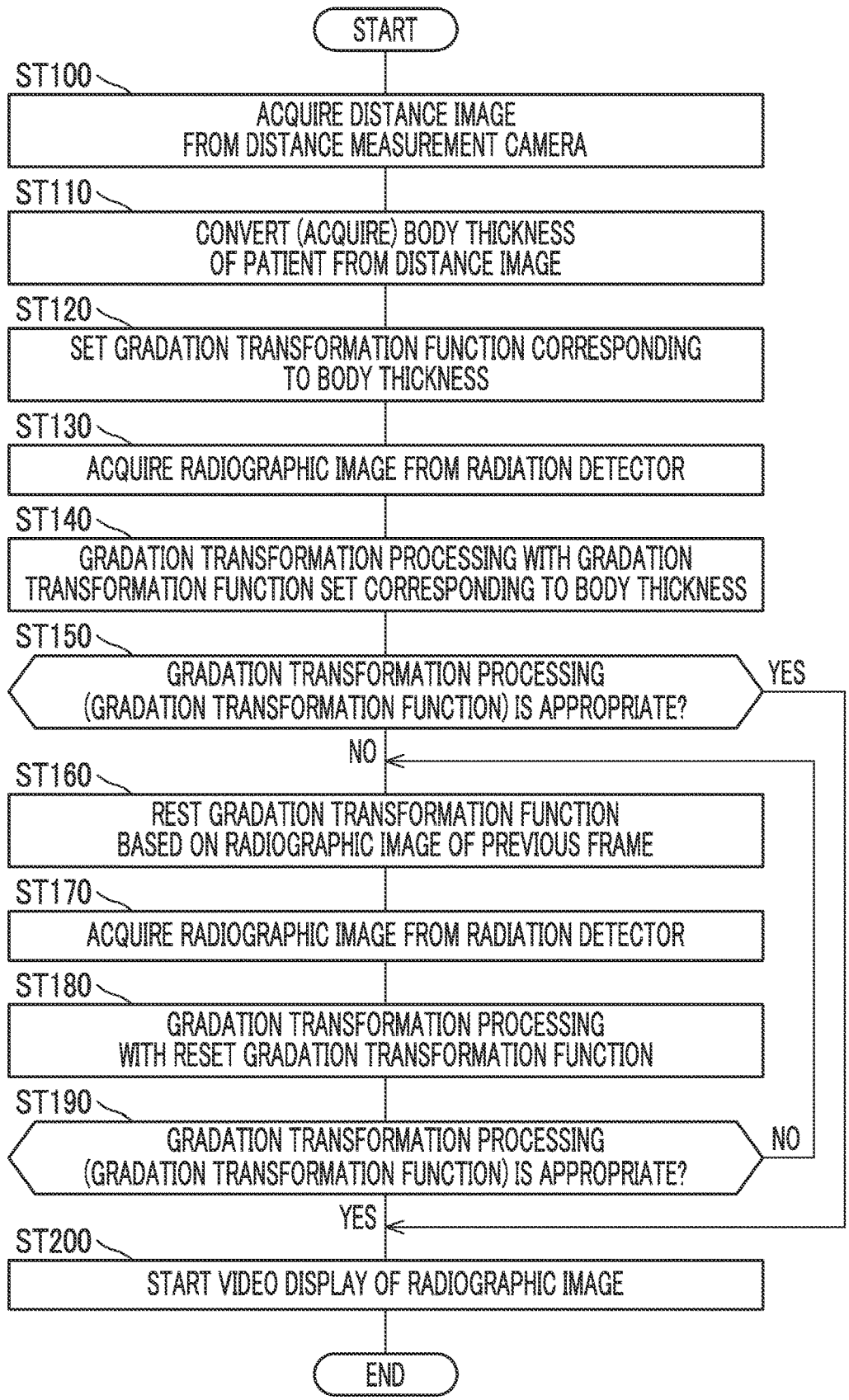
FIG. 20 is a flowchart showing a processing procedure of a processing apparatus.

Next, the operation of the above-described configuration will be described referring to a flowchart of FIG. 20. In a case where the first operation program 75 is activated, as shown in FIG. 12, the CPU 67 of the console 11 functions as the radiation source controller 80, the collimator controller 81, the distance measurement camera controller 82, the distance image acquisition unit 83, the detector controller 84, the radiographic image acquisition unit 85, the imaging instruction reception unit 86, and the display controller 87. In a case where the second operation program 76 is activated, as shown in FIG. 12, the FPGA 68 of the console 11 functions as the image processing unit 90.

As shown in FIG. 8, prior to radioscopy, the imaging menu corresponding to the imaging order is selected by the operator OP, and accordingly, the irradiation conditions are set in the voltage generator 41 by the radiation source controller 80. The adjustment of the opening degree of the emission opening of the collimator 31 is performed by the collimator controller 81. Subsequently, positioning of the radiation source 30, the radiation detector 33, and the patient P is performed by the operator OP. Thereafter, the foot switch 22 is depressed by the operator OP, and radioscopy is started.

Before radioscopy is started, as shown in FIG. 9, under the control of the distance measurement camera controller 82, the imaging operation of the distance image 55 is performed by the distance measurement camera 32 in synchronization with the timing at which the radiation detector 33 outputs the offset correction image 45O. The distance image 55 is transmitted from the distance measurement camera 32 to the console 11 and is acquired with the distance image acquisition unit 83 (Step ST100).

As shown in FIG. 13, the distance image 55 is output from the distance image acquisition unit 83 to the body thickness conversion unit 100 of the image processing unit 90. In the body thickness conversion unit 100, the body thickness BT is converted from the distance image 55 as shown in FIG. 7 (Step ST110). With this, the body thickness BT is acquired. The body thickness BT is output from the body thickness conversion unit 100 to the setting unit 101. Step ST110 is an example of "body thickness acquisition processing" according to the technique of the present disclosure.

As shown in FIGS. 13, and 16 to 19, the gradation transformation function 104I is set corresponding to the body thickness BT by the setting unit 101 (Step ST120). In this case, the default gradation transformation function 104D having a linear shape is corrected corresponding to the body thickness BT, and the gradation transformation function 104I having an S-curved shape is generated. The gradation transformation function 104I is output from the setting unit 101 to the gradation transformation processing unit 102. Step ST120 is an example of "setting processing" according to the technique of the present disclosure.

In a case where radioscopy is started, as shown in FIG. 9, the irradiation of the radiation R from the radiation source 30 is performed in a pulsed manner under the control of the radiation source controller 80. The detection operation is repeated by the radiation detector 33 in synchronization with the irradiation of the radiation R under the control of the detector controller 84. With this, the radiographic image 45 is output from the radiation detector 33. The radiographic image 45 is transmitted from the radiation detector 33 to the console 11 and is acquired with the radiographic image acquisition unit 85 (Step ST130). Step ST130 is an example of "image acquisition processing" according to the technique of the present disclosure.

The radiographic image 45 is output from the radiographic image acquisition unit 85 to the image processing unit 90. Then, in the image processing unit 90, the offset correction processing and the like using the offset correction image 45O is executed to the radiographic image 45. By the gradation transformation processing unit 102, the gradation transformation processing is executed to the radiographic image 45 of the first frame with the gradation transformation function 104I set by the setting unit 101 (Step ST140). The radiographic image 45 subjected to the gradation transformation processing is output from the gradation transformation processing unit 102 to the evaluation unit 103. Step ST140 is an example of "image processing" according to the technique of the present disclosure.

The evaluation unit 103 evaluates whether or not the gradation transformation processing by the gradation transformation processing unit 102 is appropriate (Step ST150). In a case where evaluation is made that the gradation transformation processing is appropriate (in Step ST150, YES), the radiographic image 45 after the gradation transformation processing is subjected to the noise reduction processing, and then, is output from the image processing unit 90 to the display controller 87. Then, the radiographic image 45 is displayed on the operator monitor 21 and is provided for observation of the operator OP under the control of the display controller 87. With this, the video display of the radiographic image 45 is started (Step ST200).

In a case where the evaluation unit 103 evaluates that the gradation transformation processing is not appropriate (in Step ST150, NO), the setting unit 101 resets the gradation transformation function 104 based on the radiographic image 45 of the previous frame (Step ST160). The reset gradation transformation function 104 is output from the setting unit 101 to the gradation transformation processing unit 102.

Similarly to Step ST130, the radiographic image acquisition unit 85 acquires the radiographic image 45 (Step ST170). The radiographic image 45 is output from the radiographic image acquisition unit 85 to the image processing unit 90, and is subjected to the gradation transformation processing by the gradation transformation processing unit 102 with the gradation transformation function 104 reset by the setting unit 101 (Step ST180). The processing of Steps ST160 to ST180 is repeatedly executed while the evaluation unit 103 does not evaluate that the gradation transformation processing is appropriate (in Step ST190, NO). In a case where the evaluation unit 103 evaluates that the gradation transformation processing is appropriate (in Step ST190, YES), similarly to a case where determination of YES is made in Step ST150, the radiographic image 45 after the gradation transformation processing is output from the image processing unit 90 to the display controller 87, and is displayed on the operator monitor 21 and provided for observation of the operator OP under the control of the display controller 87. With this, the video display of the radiographic image 45 is started (Step ST200). Similarly to Step ST130, Step ST170 is an example of "image acquisition processing" according to the technique of the present disclosure.

As described above, the CPU 67 of the console 11 functions as the radiographic image acquisition unit 85. The FPGA 68 of the console 11 functions as the image processing unit 90. The image processing unit 90 has the body thickness conversion unit 100, the setting unit 101, and the gradation transformation processing unit 102. The body thickness conversion unit 100 converts the body thickness BT from the distance image 55 imaged by the distance measurement camera 32 to acquire the body thickness BT. The setting unit 101 sets the gradation transformation function 104I for use in the gradation transformation processing to the radiographic image 45 corresponding to the body thickness BT. The radiographic image acquisition unit 85 acquires the radiographic image 45 output from the radiation detector 33 in radioscopy. The gradation transformation processing unit 102 starts the gradation transformation processing with the gradation transformation function 104I set by the setting unit 101.

Figure 21:
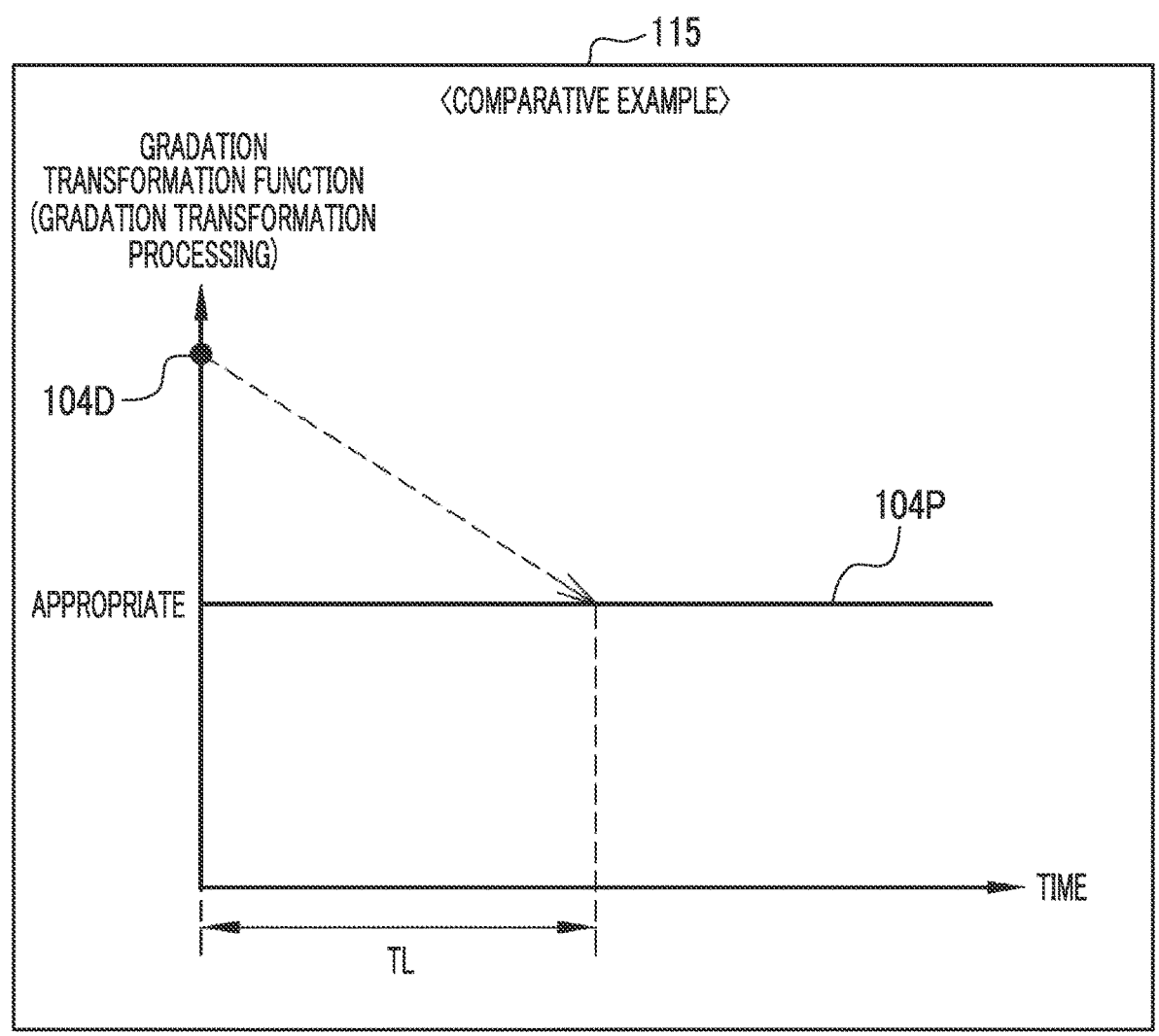
FIG. 21 is a graph showing the outline of gradation transformation processing in the related art.

FIG. 21 is a graph 115 showing the outline of gradation transformation processing in the related art shown as a comparative example. In the related art, the default gradation transformation function 104D is set first regardless of the body thickness BT. For this reason, there is a case where the default gradation transformation function 104D is significantly far from an appropriate gradation transformation function 104P. In this case, a comparatively long time TL is needed from when the start of radioscopy is instructed by the foot switch 22 until the gradation transformation processing converges into an appropriate state and the video display of the radiographic image 45 is started. There is also case where the default gradation transformation function 104D is excessively far from the appropriate gradation transformation function 104P, the gradation transformation processing does not converge into an appropriate state until a specified time, and an error occurs.

Figure 22:
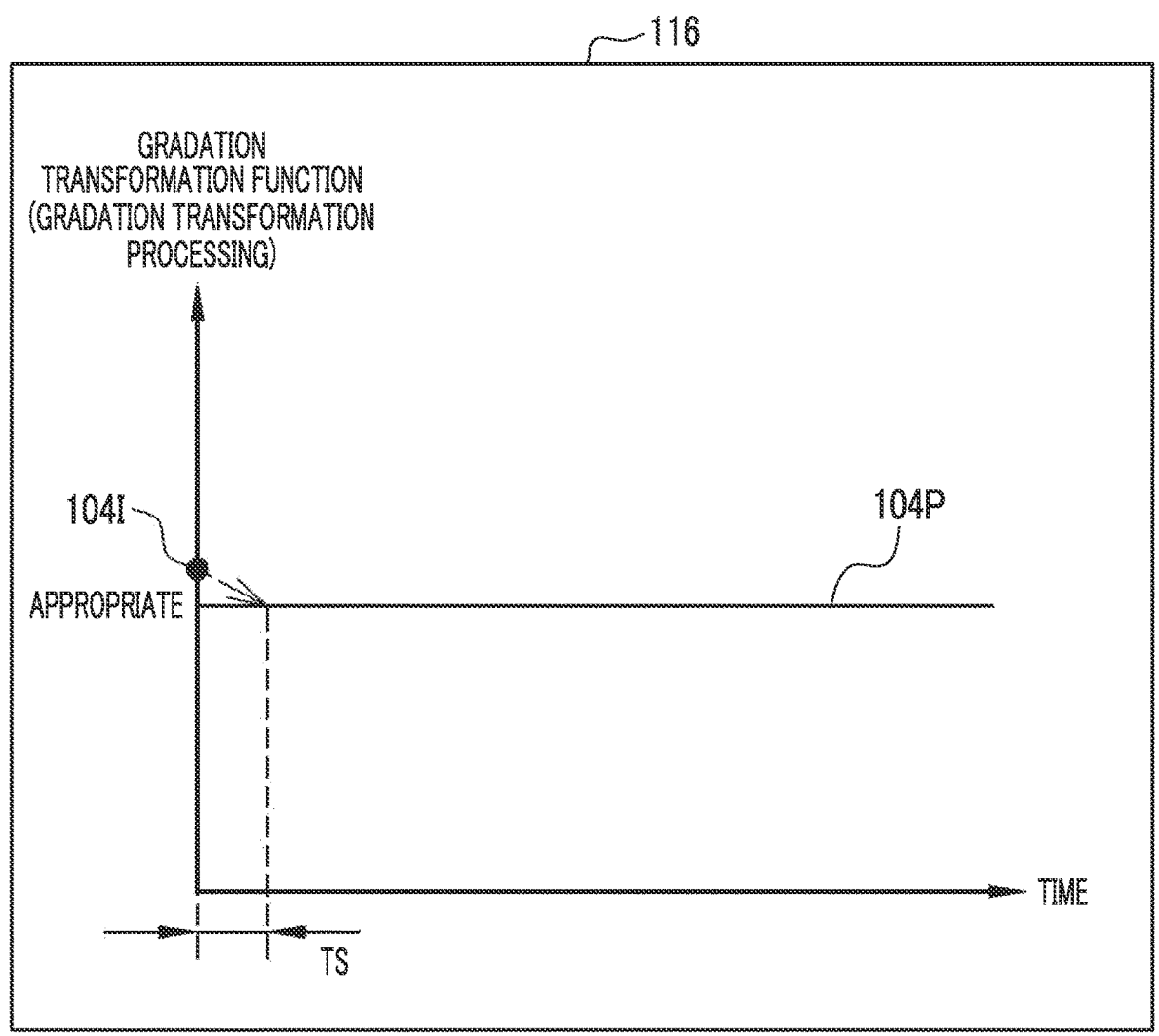
FIG. 22 is a graph showing the outline of gradation transformation processing according to the technique of the present disclosure.

In contrast, as the graph 116 shown in FIG. 22, in the technique of the present disclosure, the gradation transformation function 104I corresponding to the body thickness BT is set first. A difference between the gradation transformation function 104I and the appropriate gradation transformation function 104P is slightly small compared to the default gradation transformation function 104D. For this reason, a time TS needed from when the start of radioscopy is instructed by the foot switch 22 until the gradation transformation processing converges into an appropriate state and the video display of the radiographic image 45 is started is considerably reduced compared to the time TL in a case of FIG. 21. Accordingly, according to the technique of the present disclosure, it is possible to reduce a time needed from when radioscopy is started until the gradation transformation processing becomes appropriate.

In radioscopy, for example, there is a case where the irradiation of the radiation R is stopped once and the posture of the patient P is changed several times, such as orthopedic reduction. In a case where the body thickness BT is frequently changed during the operation in this way, in the related art, it is necessary to wait for a comparatively long time until the gradation transformation processing converges into an appropriate state and the video display of the radiographic image 45 is started, making the operator OP feel stress.

In contrast, in the technique of the present disclosure, as shown in graphs 116A and 116B of FIG. 23, even though a posture of the patient P is changed and the body thickness BT is changed, a long time is not needed until the gradation transformation processing converges into an appropriate state and the video display of the radiographic image 45 is started. For this reason, the operator OP can perform an operation without feeling stress.

In the gradation transformation function 104I, as the body thickness BT is thinner, the setting unit 101 increases the range RH_O of the output pixel value with respect to the range RH_I where the input pixel value relatively high, more than the range RL_O of the output pixel value with respect to the range RL_I where the input pixel value is relatively low. For this reason, it is possible to increase the contrast of the range R_ROI of the pixel value considered to represent the internal structure of the body of the patient P in a case where the body thickness BT is thin, in the radiographic image 45, and to provide the operator OP with an easier-to-observe radiographic image 45.

In the gradation transformation function 104I, as the body thickness BT is thicker, the setting unit 101 increases the range RL_O of the output pixel value with respect to the range RL_I where the input pixel value is relatively low, more than the range RH_O of the output pixel value with respect to the range RH_I where the input pixel value is relatively high. For this reason, it is possible to increase the contrast of the range R_ROI of the pixel value considered to represent the internal structure of the body of the patient P in a case where the body thickness BT is thick, in the radiographic image 45, and to provide the operator OP with an easier-to-observe radiographic image 45.

The setting unit 101 corrects the default gradation transformation function 104D corresponding to the body thickness BT to generate the gradation transformation function 104I. Specifically, the setting unit 101 generates the gradation transformation function 104I having an S-curved shape from the default gradation transformation function 104D having a linear shape. For this reason, it is possible to simply generate the gradation transformation function 104I corresponding to the body thickness BT.

The distance measurement camera controller 82 makes the distance measurement camera 32 measure the body thickness BT of the patient P in a case where the irradiation of the radiation R is not performed. As described above, in radioscopy, there is a case where the irradiation of the radiation R is stopped once and the posture of the patient P is changed several times, such as orthopedic reduction. For example, in a case where the irradiation of the radiation R is not performed, and in a case where the distance measurement camera 32 is made to measure the body thickness BT of the patient P, even though the posture of the patient P is changed while the irradiation of the radiation R is stopped once, it is possible to obtain the body thickness BT corresponding to the changed posture.

The distance measurement camera controller 82 makes the distance measurement camera 32 measure the body thickness BT of the patient P in synchronization with the timing at which the radiation detector 33 outputs the offset correction image 45O. The timing at which the radiation detector 33 outputs the offset correction image 45O is inevitably a timing at which the irradiation of the radiation R is not performed. The detection interval DI at which the radiation detector 33 outputs the offset correction image 45O is comparatively frequent. For this reason, in a case where the distance measurement camera 32 is made to measure the body thickness BT of the patient P in synchronization with the timing at which the radiation detector 33 outputs the offset correction image 45O, it is possible to reliably measure the body thickness BT before radioscopy.

As a "body thickness measurement sensor" according to the technique of the present disclosure, the distance measurement camera 32 that is attached to the radiation source 30 and measures the distance between the radiation source 30 and the body surface of the patient P using the TOF system is used. As the body thickness measurement sensor, a stereo camera that measures a distance to an object from an image imaged with two cameras having parallax may be used, instead of the illustrated distance measurement camera 32. Alternatively, an ultrasound sensor that emits an ultrasonic wave from an ultrasound transducer to measure a distance to an object based on an ultrasound echo reflected from the object may be used. The distance measurement camera 32 is more preferable because the distance between the radiation source 30 and the body surface of the patient P can be more accurately measured and a simple device configuration can be made, compared to the stereo camera, the ultrasound sensor, or the like.

The timing at which the distance measurement camera 32 is made to measure the body thickness BT is not limited to the exemplified timing at which the radiation detector 33 outputs the offset correction image 45O. The distance measurement camera 32 may be made to measure the body thickness BT at regular intervals simply while the depression of the foot switch 22 is released.

The gradation transformation function 104I is not limited to the illustrated S-curved shape. An S-polygonal line shape may be applied. In a case of the gradation transformation function 104I having an S-polygonal line shape, a difference in contrast of a portion having a slope of 0 is eliminated and distinction is confused, and thus, the gradation transformation function 104I having an S-curved shape is more preferable.

The default gradation transformation function 104D is also not limited to the illustrated linear shape. An S-curved shape may be applied.

Although the distance between the radiation source 30 and the surface of the imaging table 20 is invariable, the present disclosure is not limited thereto. A configuration may be made in which the distance between the imaging table 20 and the radiation source 30 is variable.

To rapidly converge ABC by the radiation source controller 80, the irradiation conditions may be changed depending on the body thickness BT.

The radiographic image 45 may be equally divided into a plurality of regions, the gradation transformation function 104I or 104 may be set individually to each region, and the gradation transformation processing may be executed for each region.

Second Embodiment

Figure 24:
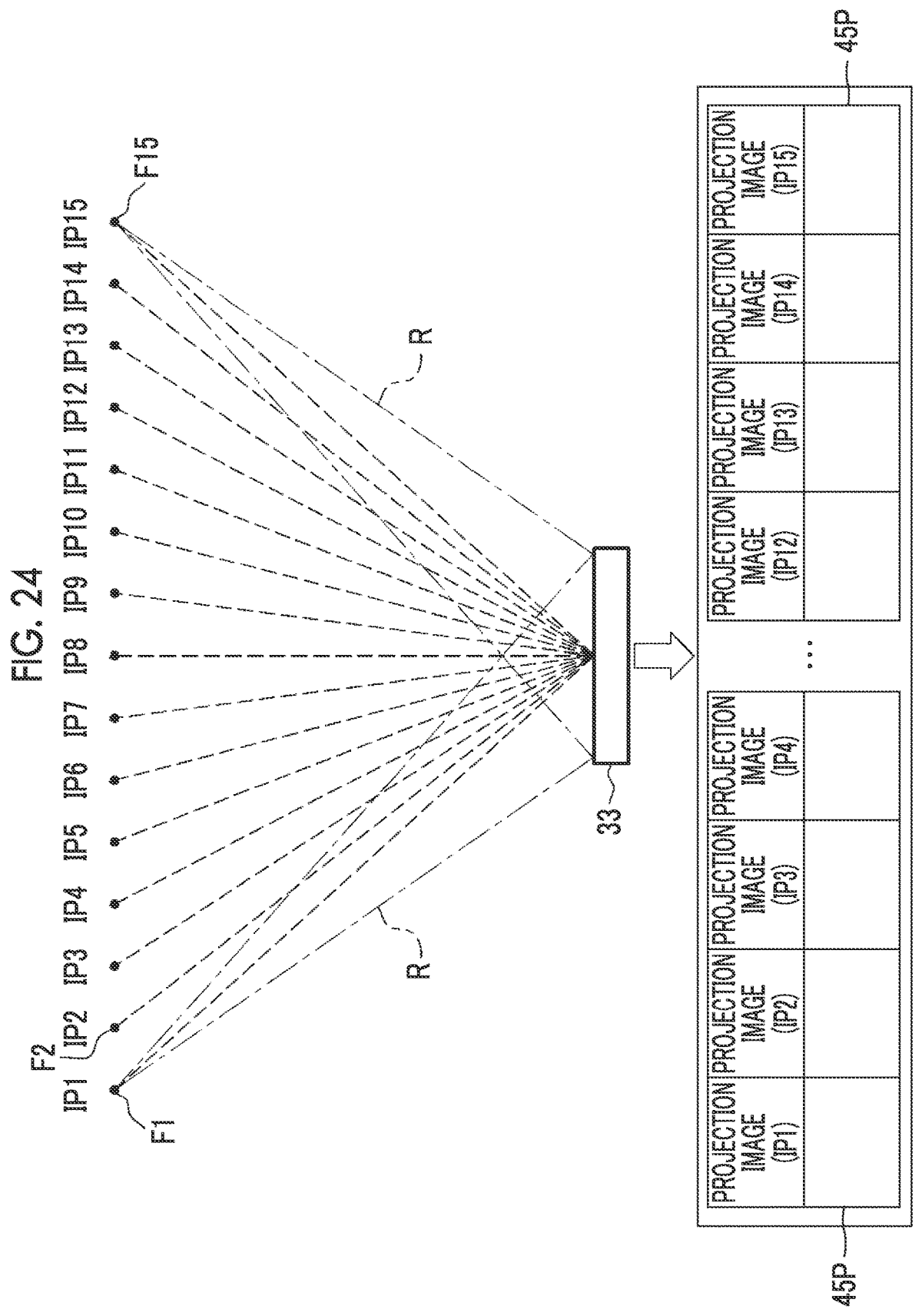
Figure 25:
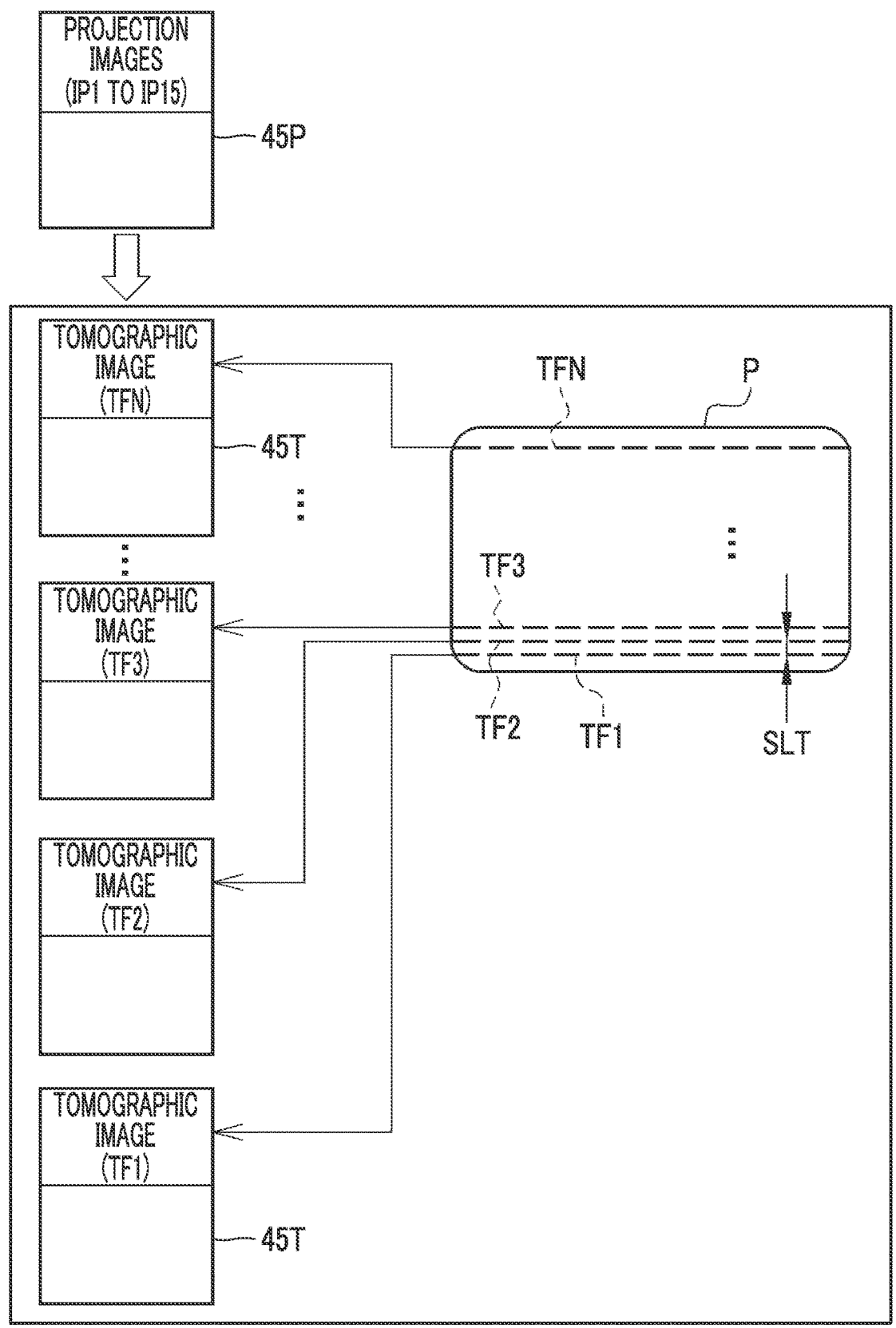
FIG. 25 is a diagram showing a manner of reconfiguring tomographic images from a plurality of projection images obtained by tomosynthesis imaging.
Figure 26:
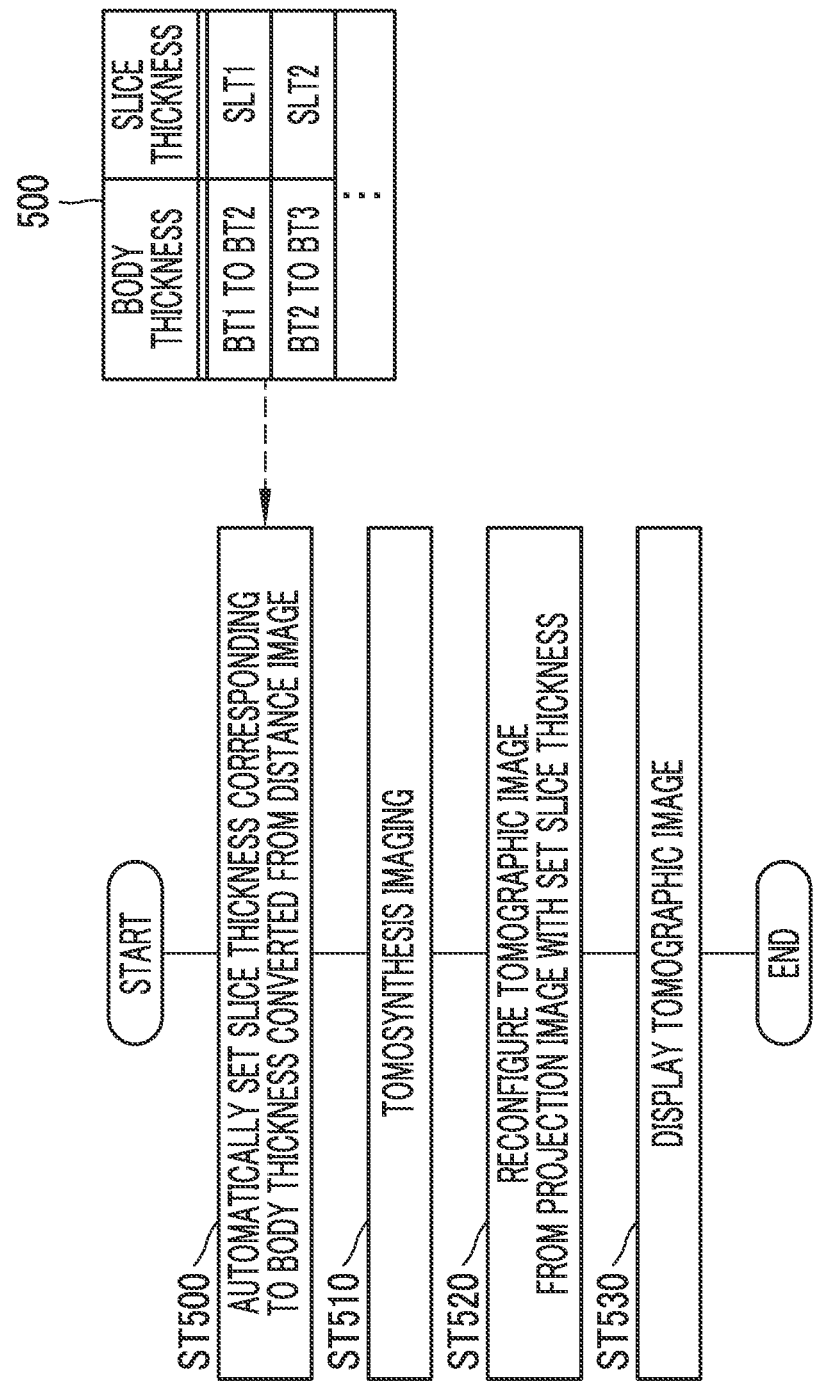
FIG. 26 is a flowchart showing a procedure of a second embodiment.

In a second embodiment shown in FIGS. 24 to 26, tomosynthesis imaging is performed in addition to radioscopy.

As shown in FIG. 24, tomosynthesis imaging is imaging where the radiation source 30 is sequentially moved to a plurality of irradiation positions IP arranged at equal intervals along the longitudinal direction of the imaging table 20, the irradiation of the radiation R is performed from a plurality of focuses F corresponding to the respective irradiation positions IP to the radiation detector 33, and the radiographic image 45 (hereinafter, referred to as a projection image 45P) is output from the radiation detector 33 each time. In tomosynthesis imaging, the radiation detector 33 is placed at the center of the irradiation position IP. FIG. 24 shows an example of tomosynthesis imaging where the irradiation of the radiation R is performed from 15 focuses F1 to F15 corresponding to 15 irradiation positions IP1 to IP15 centering on an irradiation position IP8, and 15 projection images 45P are obtained.

As shown in FIG. 25, the image processing unit 90 reconfigures tomographic images 45T corresponding to tomographic planes TF1 to TFN of the patient P from the projection images 45P obtained through tomosynthesis imaging shown in FIG. 24 using a known method, such as a filtered back projection method. The image processing unit 90 reconfigures the tomographic image 45T with a slice thickness SLT set in advance. The display controller 87 displays the tomographic images 45T on the operator monitor 21.

As shown in FIG. 26, in the console 11, the slice thickness SLT corresponding to the body thickness BT of the patient P converted from the distance image 55 is automatically set with reference to a slice thickness table 500 (Step ST500). In the slice thickness table 500, the slice thickness SLT of a greater value is registered as the body thickness is thicker. The slice thickness table 500 is stored in the storage device 65.

After the slice thickness SLT is automatically set, tomosynthesis imaging shown in FIG. 24 is performed (Step ST510). With this, a plurality of projection image 45P corresponding to the respective irradiation positions IP are obtained. Then, as shown in FIG. 25, the tomographic image 45T is reconfigured from the projection image 45P with the automatically set slice thickness SLT by the image processing unit 90 (Step ST520). The reconfigured tomographic image 45T is displayed on the operator monitor 21 under the control of the display controller 87 (Step ST530).

Figure 27:
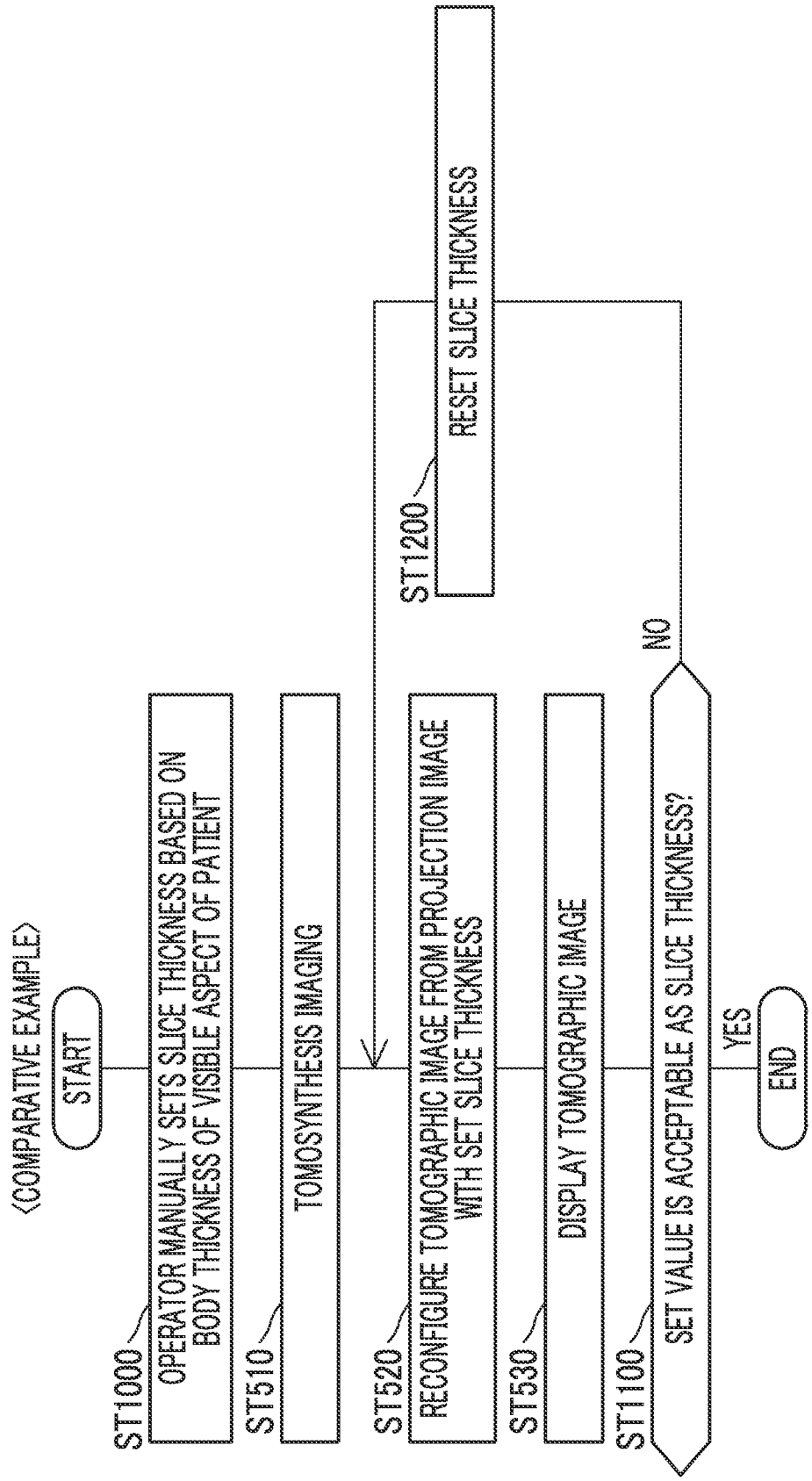
FIG. 27 is a flowchart showing a procedure in the related art as a comparative example.

FIG. 27 is a flowchart showing a procedure in the related art as a comparative example. In the related art, the operator OP manually sets a slice thickness SLT through the input device 13 based on a body thickness BT of a visible aspect of the patient P (Step ST1000). For this reason, the operator OP determines whether or not a set value is acceptable as the slice thickness SLT by the tomographic image 45T displayed on the operator monitor 21 (Step ST1100). Then, in a case where the set value is not acceptable as the slice thickness SLT (in Step ST1100, NO), the operator OP resets the slice thickness SLT (Step ST1200), and the processing of Steps ST520 and ST530 is repeated. A time of about several minutes is needed in reconfiguring the tomographic image 45T from the projection image 45P after the slice thickness SLT is reset. Therefore, in the related art, there is a case where a time is needed to obtain a tomographic image 45T at a desired slice thickness SLT.

In contrast, in the second embodiment, as shown in FIG. 26, the slice thickness SLT is automatically set depending on the body thickness BT of the patient P converted from the distance image 55. Accordingly, a lot of labor is not needed to manually set the slice thickness SLT unlike the related art, and a lot of time is not needed until the tomographic image 45T of a desired slice thickness SLT is obtained.

Figure 28:
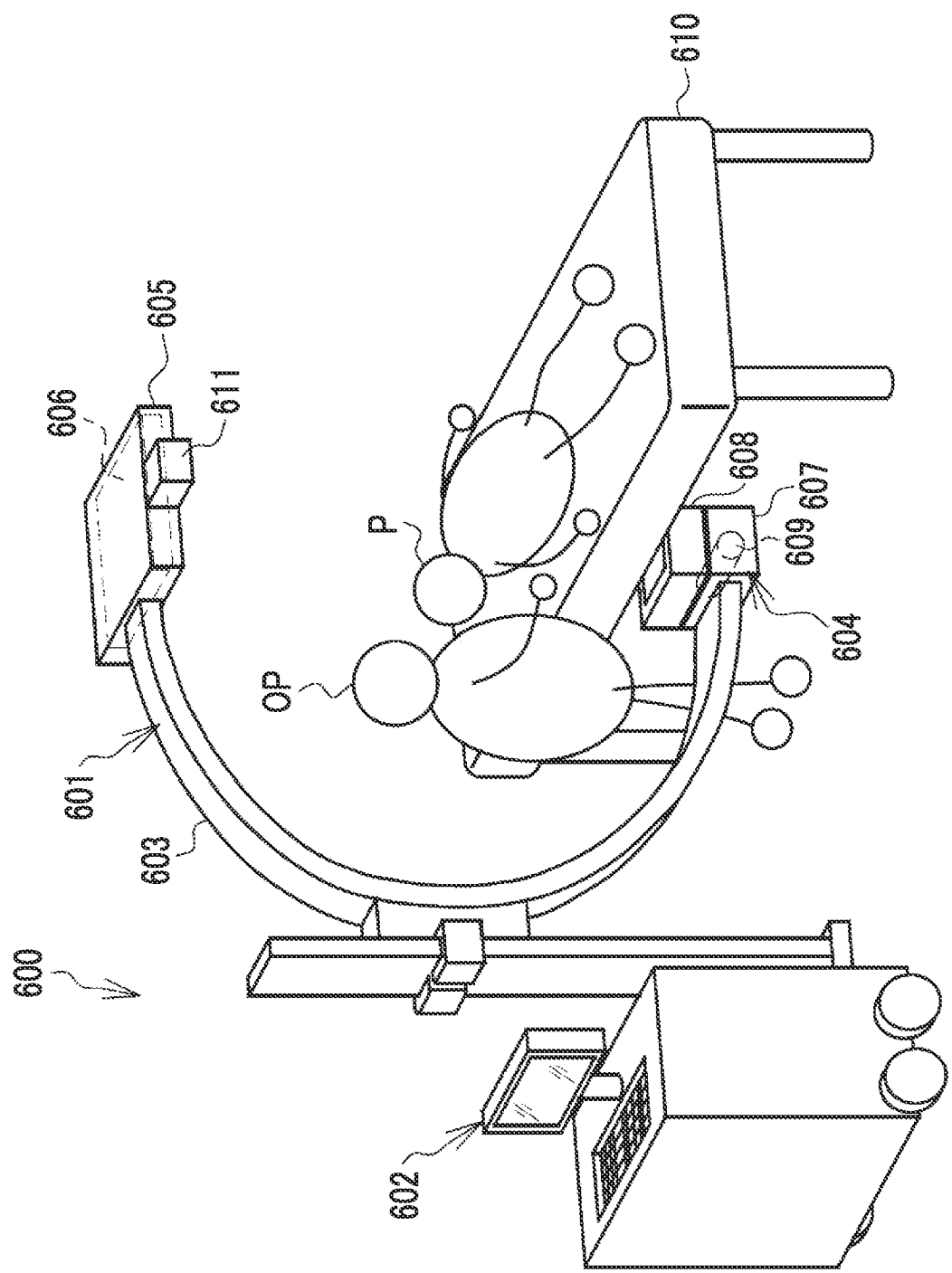
FIG. 28 is a diagram showing a radioscopy system comprising a C-arm type radioscopy apparatus.

The technique of the present disclosure may be applied to a radioscopy system 600 shown in FIG. 28. The radioscopy system 600 comprises a radioscopy apparatus 601 and a console 602 integrated into the radioscopy apparatus 601. The radioscopy apparatus 601 is a so-called C-arm type in which a radiation generation unit 604 is attached to one end of a C-arm 603, and a radiation detector 606 is incorporated in a holder 605 provided in the other end of the C-arm 603. The radiation generation unit 604 has a radiation source 607 and a collimator 608. The radiation source 607 has a radiation tube 609. In FIG. 28, a foot switch and an operator monitor are omitted.

In a case of the C-arm type radioscopy apparatus 601, normally, to reduce useless exposure to the operator OP, radioscopy is performed in an under-tube posture shown in FIG. 28 in which the radiation source 607 is positioned below the patient P and the radiation detector 606 are positioned above the patient P with a bed 610 sandwiched between the radiation source 607 and the radiation detector 606. For this reason, in the radioscopy apparatus 601, a distance measurement camera 611 is attached to the holder 605, not the radiation generation unit 604. In this case, it is possible to calculate the body thickness BT by subtracting a distance between the distance measurement camera 611 and the shortest point of the body surface of the patient P from a distance between the distance measurement camera 611 and a surface of the bed 610.

In the C-arm type radioscopy apparatus 601, although it is extremely rare, there is a case where radioscopy is performed in an over-tube posture in which the radiation source 607 is positioned above the patient P and the radiation detector 606 is positioned below the patient P. To cope with radioscopy in the over-tube posture, the distance measurement camera 611 may be attached to not only the holder 605 but also the radiation generation unit 604.

Although the patient P is exemplified as the subject, the present disclosure is not limited thereto. A pet, such as a dog or a cat, or a domestic animal, such as a horse or cattle, may be a subject.

The hardware configuration of the computer constituting the console 11 can be modified in various ways. The console 11 can also be constituted of a plurality of computers separated as hardware for the purpose of improving processing capability and reliability. For example, the functions of the respective units 80 to 87 constructed in the CPU 67 and the function of the image processing unit 90 constructed in the FPGA 68 are distributed to two computers. In this case, the console 11 is constituted of two computers.

In this way, the hardware configuration of the computer of the console 11 can be appropriately changed depending on required performance, such as processing capability, safety, or reliability. Not only hardware but also an application program, such as the first operation program 75 and the second operation program 76, can be of course duplicated or distributed and stored in a plurality of storage devices for the purpose of ensuring safety and reliability.

As the hardware structures of processing units that execute various kinds of processing, such as the radiation source controller 80, the collimator controller 81, the distance measurement camera controller 82, the distance image acquisition unit 83, the detector controller 84, the radiographic image acquisition unit 85, the imaging instruction reception unit 86, the display controller 87, the image processing unit 90, the body thickness conversion unit 100, the setting unit 101, and the gradation transformation processing unit 102, and the evaluation unit 103, various processors described below can be used. Various processors include at least one of a programmable logic device (PLD) that is a processor capable of changing a circuit configuration after manufacture, such as the FPGA 68, a dedicated electric circuit that is a processor having a circuit configuration dedicatedly designed for executing specific processing, such as an application specific integrated circuit (ASIC), or the like, in addition to the CPU 67 that is a general-purpose processor executing software (first operation program 75) to function as various processing units.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

The technique of the present disclosure can also be appropriately combined with at least one of various embodiments or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A processing apparatus that is used for a radioscopy apparatus including a radiation source configured to continuously irradiate a subject with radiation and a radiation detector configured to detect the radiation transmitted through the subject to output a radiographic image, the processing apparatus comprising:
    at least one processor,
    the processor is configured to
    (1) acquire a body thickness of the subject measured by a body thickness measurement sensor,
    (2) set a gradation transformation function for use in gradation transformation processing to the radiographic image corresponding to the body thickness, gradation transformation processing processes an input pixel value which is a pixel value of the radiographic image and outputs as an output pixel value,
    (3) acquire the radiographic image output from the radiation detector, and
    (4) execute the gradation transformation processing with the set gradation transformation function,
    (5) derive a spatial frequency-strength characteristic of the radiographic image after the gradation transformation processing, and
    (6) in a case in which a peak of the spatial frequency-strength characteristic is equal to or greater than a threshold frequency set or calculated in advance, output the radiographic image after the gradation transformation processing, and in a case in which the peak is less than the threshold frequency, reset the gradation transformation function and repeat the process from (3).

2. The processing apparatus according to claim 1, wherein the processor is configured to, in the gradation transformation function, as the body thickness is thinner, increase a range of the output pixel value with respect to a range where the input pixel value is relatively high, more than a range of an output pixel value with respect to a range where an input pixel value is relatively low.

3. The processing apparatus according to claim 1, wherein the processor is configured to, in the gradation transformation function, as the body thickness is thicker, increase a range of the output pixel value with respect to a range where the input pixel value is relatively low, more than a range of an output pixel value with respect to a range where an input pixel value is relatively high.

4. The processing apparatus according to claim 1, wherein the processor is configured to correct a default gradation transformation function corresponding to the body thickness to generate the gradation transformation function to be set.

5. The processing apparatus according to claim 1, wherein the processor is configured to make the body thickness measurement sensor measure the body thickness in a case where the irradiation of the radiation is not performed.

6. The processing apparatus according to claim 1, wherein the body thickness measurement sensor is a distance measurement camera that outputs a distance image representing a distance to a surface of an object using a time-of-flight system, and
the processor is configured to convert the body thickness from the distance image.

7. The processing apparatus according to claim 4, wherein the processor is configured to generate the gradation transformation function having an S-curved shape from the default gradation transformation function having a linear shape.

8. The processing apparatus according to claim 5, wherein the processor is configured to make the body thickness measurement sensor measure the body thickness in synchronization with a timing at which the radiation detector outputs the radiographic image for offset correction.

9. A method of operating a processing apparatus that is used for a radioscopy apparatus the method comprising:
    continuously irradiating radiation from a radiation source to a subject; and
    detecting the radiation transmitted through the subject using a radiation detector to output a radiographic image,
    acquiring a body thickness of the subject measured by a body thickness measurement sensor;
    setting a gradation transformation function for use in gradation transformation processing to the radiographic image corresponding to the body thickness, gradation transformation processing processes an input pixel value which is a pixel value of the radiographic image and outputs as an output pixel value;

acquiring the radiographic image output from the radiation detector;

executing the gradation transformation processing with the set gradation transformation function;

deriving a spatial frequency-strength characteristic of the radiographic image after the gradation transformation processing; and in a case in which a peak of the spatial frequency-strength characteristic is equal to or greater than a threshold frequency set or calculated in advance, output the radiographic image after the gradation transformation processing, and in a case in which the peak is less than the threshold frequency, resetting the gradation transformation function and repeating the process from the acquiring the radiographic image.

10. A non-transitory computer-readable storage medium storing an operation program for a processing apparatus that is used for a radioscopy apparatus including a radiation source configured to continuously irradiate a subject with radiation and a radiation detector configured to detect the radiation transmitted through the subject to output a radiographic image, the operation program causing a processor to execute:

(1) body thickness acquisition processing of acquiring a body thickness of the subject measured by a body thickness measurement sensor;

(2) setting processing of setting a gradation transformation function for use in gradation transformation processing to the radiographic image corresponding to the body thickness, gradation transformation processing processes an input pixel value which is a pixel value of the radiographic image and outputs as an output pixel value;

(3) image acquisition processing of acquiring the radiographic image output from the radiation detector;

(4) image processing of executing the gradation transformation processing with the set gradation transformation function;

(5) deriving a spatial frequency-strength characteristic of the radiographic image after the gradation transformation processing; and (6) in a case in which a peak of the spatial frequency-strength characteristic is equal to or greater than a threshold frequency set or calculated in advance, output the radiographic image after the gradation transformation processing, and in a case in which the peak is less than the threshold frequency, resetting the gradation transformation function and repeating the process from (3).

* * * * *